(12) United States Patent
Ram et al.

(10) Patent No.: US 10,054,563 B2
(45) Date of Patent: *Aug. 21, 2018

(54) OPTOELECTRONIC PIXEL SENSOR

(71) Applicant: RG SMART PTE. LTD., Singapore (SG)

(72) Inventors: Ayal Ram, Singapore (SG); Amir Lichtenstein, Singapore (SG); Xuan-Thang Vu, Zweibrücken (DE); Jessica Ka-Yan Law, Zweibrücken (DE); Duy Phu Tran, Zweibrücken (DE); Jannick Wilhelm, Zweibrücken (DE); Thanh Chien Nguyen, Zweibrücken (DE); Miriam Schwartz, Contwig (DE)

(73) Assignee: RGE SMART PTE. LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/087,866

(22) Filed: Mar. 31, 2016

(65) Prior Publication Data
US 2016/0290958 A1    Oct. 6, 2016

Related U.S. Application Data

(60) Provisional application No. 62/140,950, filed on Mar. 31, 2015, provisional application No. 62/140,974, (Continued)

(51) Int. Cl.
*G01N 27/414* (2006.01)
*C12Q 1/00* (2006.01)
(Continued)

(52) U.S. Cl.
CPC ......... *G01N 27/4145* (2013.01); *C12Q 1/001* (2013.01); *G01N 21/554* (2013.01);
(Continued)

(58) Field of Classification Search
CPC ............ G01N 27/4145; G01N 21/554; G01N 27/4146; G01N 33/54373; C12Q 1/001;
(Continued)

(56) References Cited

U.S. PATENT DOCUMENTS

| | | | | |
|---|---|---|---|---|
| 2008/0283875 A1* | 11/2008 | Mukasa | ................ | B82Y 10/00 257/253 |
| 2010/0323925 A1* | 12/2010 | Gabriel | ................ | B82Y 15/00 506/39 |
| 2012/0134880 A1* | 5/2012 | Kurkina | ............ | G01N 27/4146 422/82.01 |

OTHER PUBLICATIONS

Vu et al., Fabrication and application of silicon nanowire transistor arrays for biomolecular detection, 2010, Sensors and Actuators B : Chemical, vol. 144, pp. 354-360.*

(Continued)

*Primary Examiner* — Melanie Yu Brown
(74) *Attorney, Agent, or Firm* — Knobbe, Martens, Olson & Bear, LLP

(57) ABSTRACT

In some embodiments, an electrical circuit element, defined as "optoelectronic pixel", comprises at least one silicon nanowire decorated with optoelectronically active particles and open for contact with a medium for sensing; a metal electrode open for contact with said medium and used for feeding a high-frequency sinusoidal stimulation in impedance measurements and for sensing properties of said medium; implanted source and drain electrodes connected to said silicon nanowire and leaving the gate area and parts of said electrode open for contact with said medium; electrical metal contacts for connecting said pixel to an electrical circuit; and a reference electrode open for contact with said medium for creating a three-electrode-cell system and providing a constant gate potential in the circuit. In addition, some embodiments provide an optoelectronic sensor and (Continued)

wearable-patch sensor based on the array of the optoelectronic pixels, and the readout methods for these sensors.

21 Claims, 34 Drawing Sheets

Related U.S. Application Data filed on Mar. 31, 2015, provisional application No. 62/140,990, filed on Mar. 31, 2015, provisional application No. 62/141,014, filed on Mar. 31, 2015.

(51) Int. Cl.

| | |
|---|---|
| *G01N 21/552* | (2014.01) |
| *G01N 33/543* | (2006.01) |
| *H01L 31/0224* | (2006.01) |
| *H01L 31/0232* | (2014.01) |
| *H01L 31/028* | (2006.01) |
| *H01L 31/0352* | (2006.01) |
| *H01L 31/113* | (2006.01) |
| *H01L 31/16* | (2006.01) |

(52) U.S. Cl.
CPC ... *G01N 27/4146* (2013.01); *G01N 33/54373* (2013.01); *H01L 31/028* (2013.01); *H01L 31/02322* (2013.01); *H01L 31/022408* (2013.01); *H01L 31/035227* (2013.01); *H01L 31/1136* (2013.01); *H01L 31/162* (2013.01)

(58) Field of Classification Search
CPC ............ H01L 31/02322; H01L 31/162; H01L 31/028; H01L 31/035227; H01L 31/1136; H01L 31/022408
See application file for complete search history.

(56) References Cited

OTHER PUBLICATIONS

Kharitonov et al., The Use of Impedance Spectroscopy for the Characterization of Protein-Modified ISFET Devices: Application of the Method for the Analysis of Bioregonition Processes, J. Phys. Chem. B, 2001, vol. 105, pp. 4205-4213.*
M. L. Zhang, C. Q. Yi, X. Fan, K. Q. Peng, N. B. Wong, M. S. Yang, R. Q. Zhang and S. T. Lee, A surface-enhanced Raman spectroscopy substrate for highly sensitive label-free immunoassay, Appl. Phys. Lett, 92 (2008), 043116.
A. Tarasov, Silicon Nanowire Field-effect Transistors for Sensing Applications, Ph.D. thesis, Universität Basel, Basel, (2012).
D. Bavli, M. Tkachev, H. Piwonski, E. Capua, I. d. Albuquerque, D. Bensimon, G. Haran, and R. Naaman, Detection and Quantification through a Lipid Membrane Using the Molecularly Controlled Semiconductor Resistor, Langmuir 28 (2012), 1020-1028.
Y. Cui, Q. Wei, H. Park, and C. M. Lieber, Nanowire nanosensors for highly sensitive and selective detection of biological and chemical species, Science 293 (2001), 1289-1292.
J. Hahm and C. M. Lieber, Direct ultrasensitive electrical detection of DNA and DNA sequence variations using nanowire nanosensors, Nano Letters 4 (2004), 51-54.
F. Patolsky, G. Zheng, O. Hayden, M. Lakadamyali, X. Zhuang, and C. Lieber, Electrical detection of single viruses, Proceedings of the National Academy of Sciences of the United States of America 101 (2004), 14017.
F. Patolsky, G. Zheng, and C. M. Lieber, Nanowire-based biosensors, Analytical Chemistry 78 (2006), 4260-4269.
Z. Jiang, Q. Qing, P. Xie, R. Gao, and C. M. Lieber, Kinked pn junction nanowire probes for high spatial resolution sensing and intracellular recording, Nano Letters 12 (2012), 1711-1716.
R. Elnathan, M. Kwiat, A. Pevzner, Y. Engel, L. Burstein, A. Khatchtourints, A. Lichtenstein, R. Kantaev, and F. Patolsky, Biorecognition layer engineering: overcoming screening limitations of nanowire-based FET devices, Nano Letters 12 (2012), 5245-5254.
G. Zhang, J. Chua, R. Chee, A. Agarwal, S. Wong, K. Buddharaju, and N. Balasubramanian, Highly sensitive measurements of PNA-DNA hybridization using oxide-etched silicon nanowire biosensors, Biosensors and Bioelectronics 23 (2008), 1701-1707.
X. T. Vu, J. F. Eschermann, R. Stockmann, R. Ghosh Moulick, A. Offenhäusser, and S. Ingebrandt, Top-down processed silicon nanowire transistor arrays for biosensing, Phys. Status Solidi A 206(3) (2009), 426-434.
X. T. Vu, R. Stockmann, B. Wolfrum, A. Offenhäusser, and S. Ingebrandt, Fabrication and application of a microfluidic-embedded silicon nanowire biosensor chip, Phys. Status Solidi A 207(4) (2010), 850-857.
C. Ahn, A. Kulkarni, H.-U Kim, C. Shin, Y. Xu, S. Jung, H. Kim, M. Lee, and T. Kim, Light-sensitive silicon nanowire array field effect transistor for glucose detection, Nano 9(8) (2014), 1450099 (6 pages).
J.-H. Ahn, J. Yun, Y.-K. Choi, and I. Park, Palladium nanoparticle decorated silicon nanowire field-effect transistor with side-gates for hydrogen gas detection, Applied Physics Letters 104 (2014), 013508 (6 pages).
S.-W. Ryu, C.-H. Kim, J.-W. Han, C.-J. Kim, C. Jung, H. G. Park, Y.-K. Choi, Gold nanoparticle embedded silicon nanowire biosensor for applications of label-free DNA detection, Biosensors and Bioelectronics 25 (2010), pp. 2182-2185.
S. Yan, N. He, Y. Song, Z. Zhang, J. Qian, Z. Xiao, A novel biosensor based on gold nanoparticles modified silicon nanowire arrays, Journal of Electroanalytical Chemistry 641 (2010), pp. 136-140.
J. Huang, Y. Zhu, H. Zhong, X. Yang, and C. Li, Dispersed CuO Nanoparticles on a Silicon Nanowire for Improved Performance of Nonenzymatic H2O2 Detection, ACS Appl. Mater. Interfaces 6 (2014), pp. 7055-7062.

\* cited by examiner

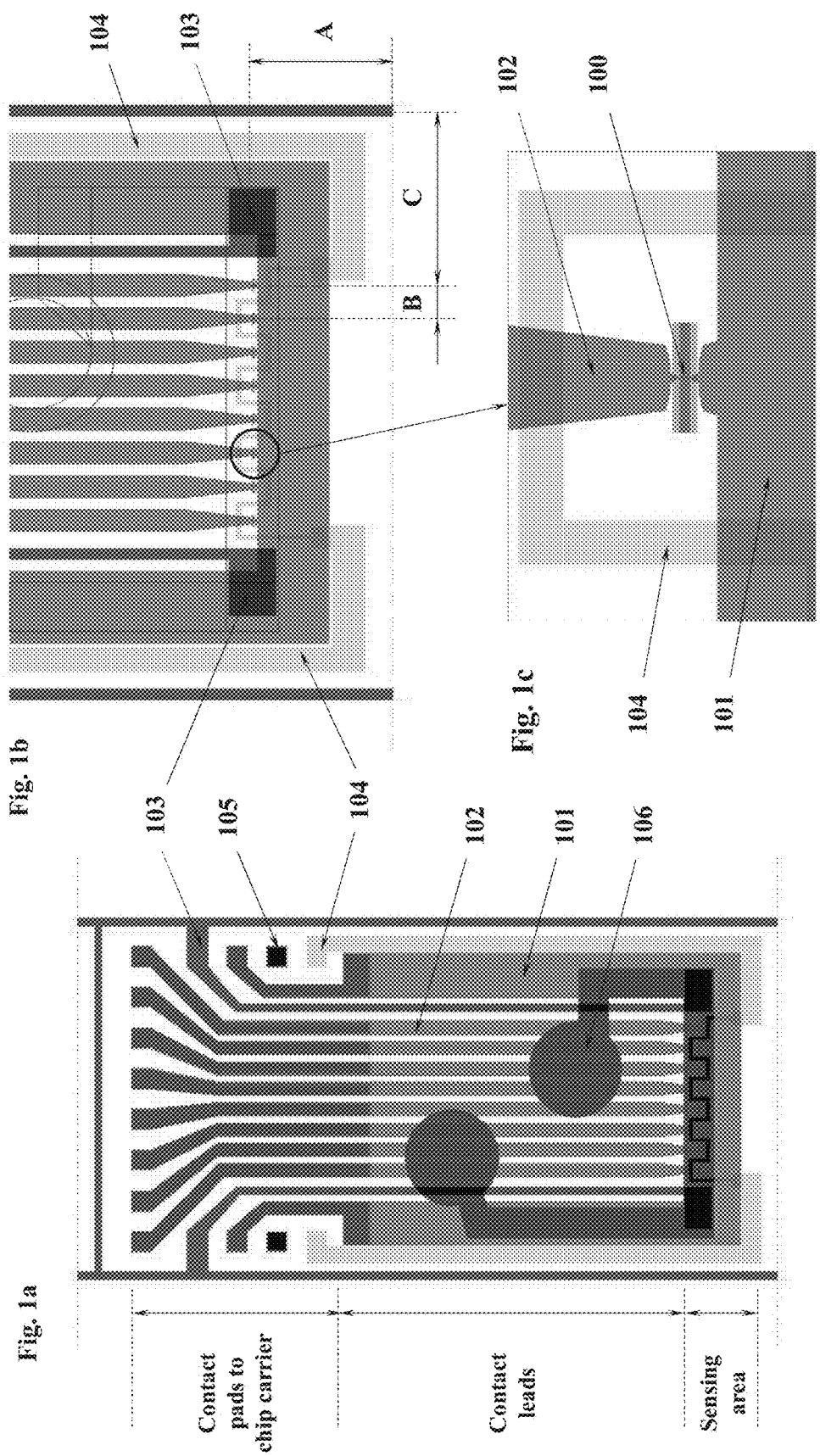

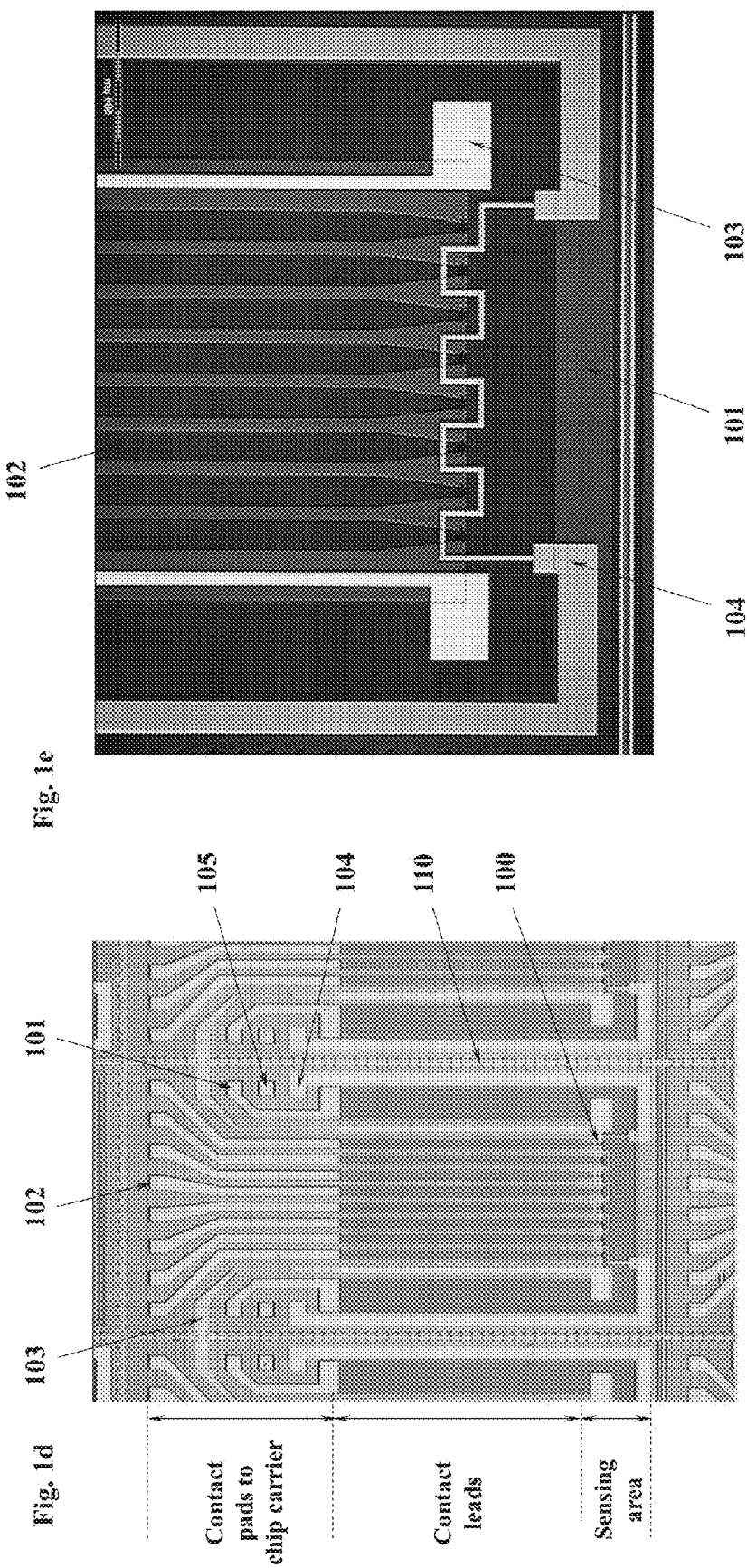

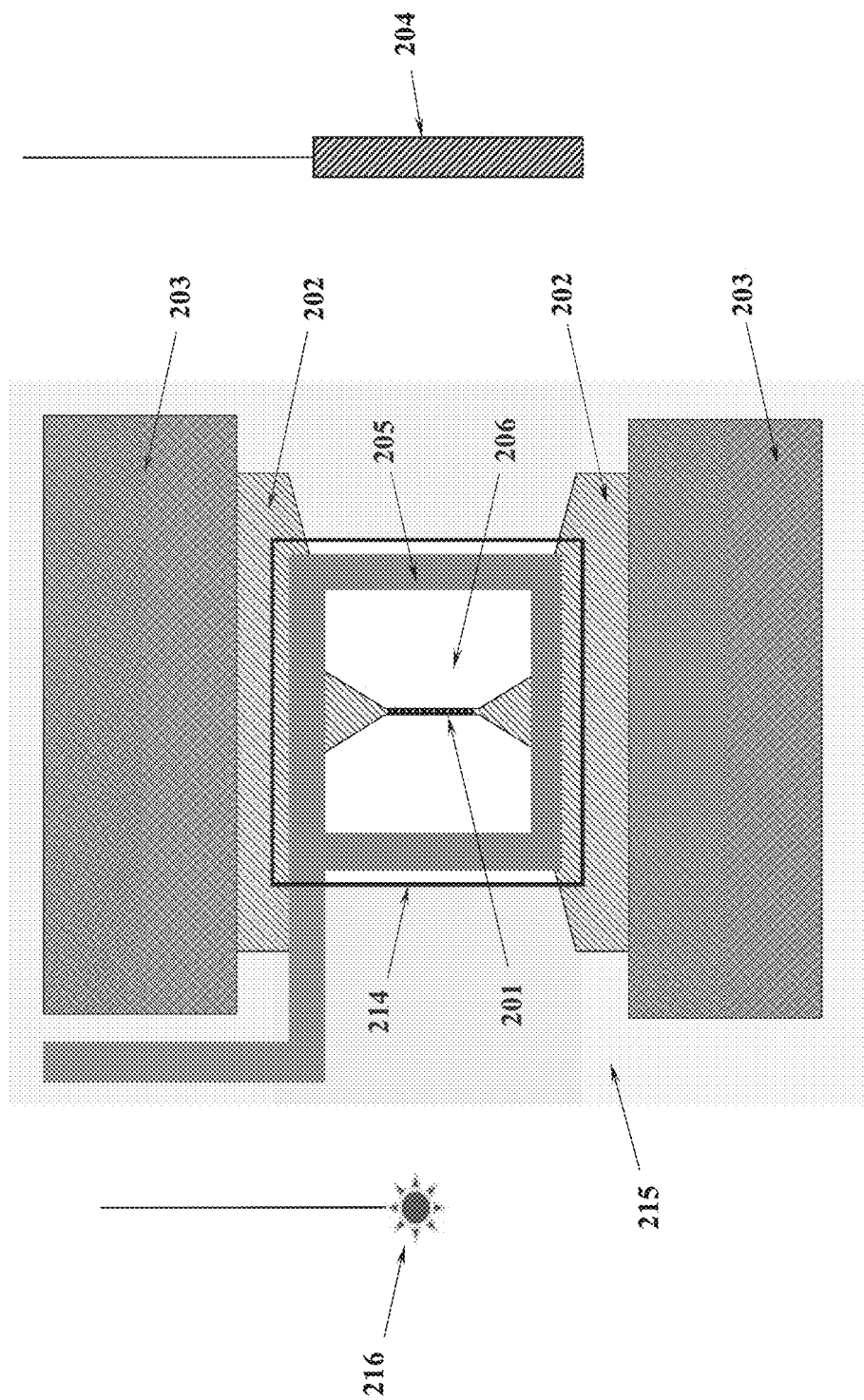

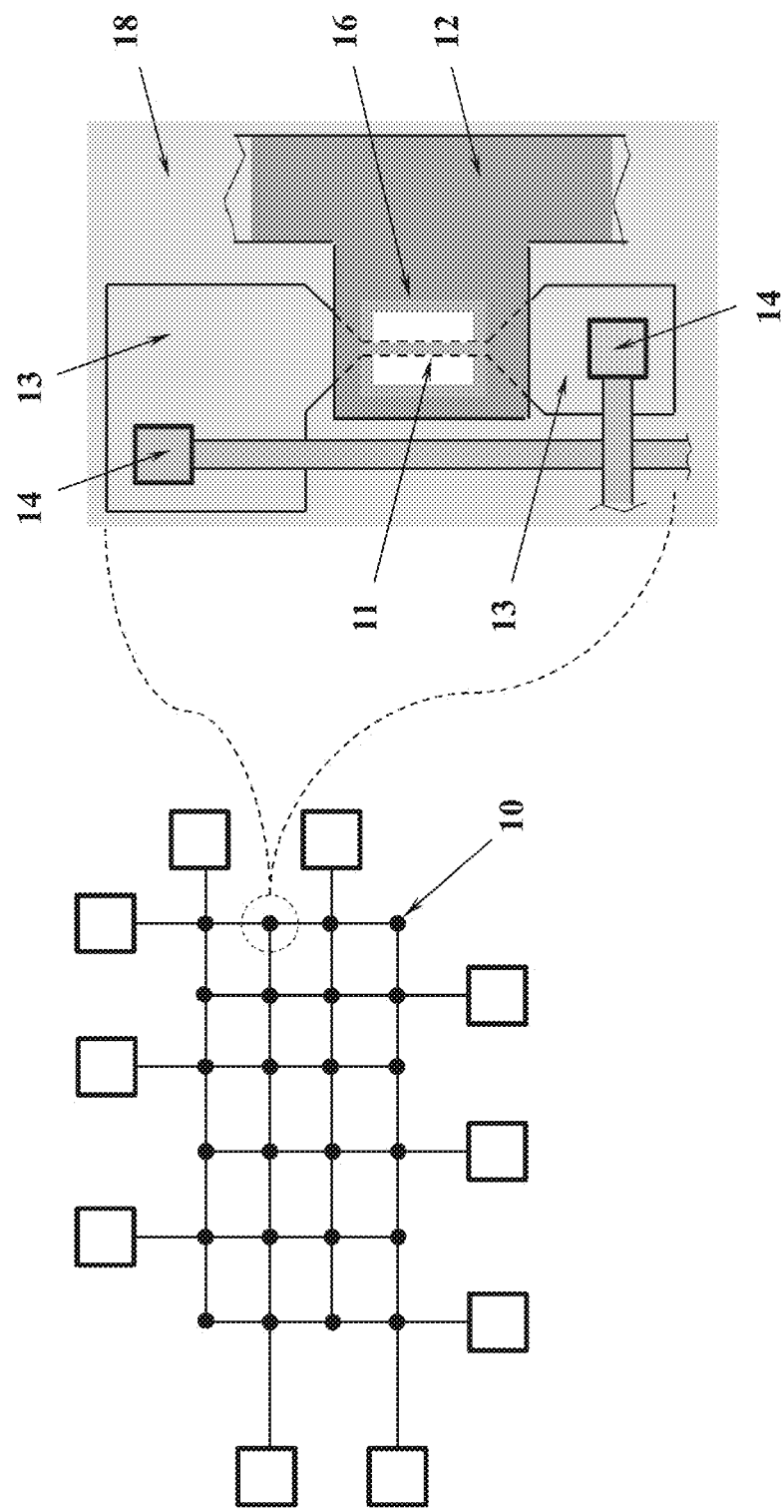

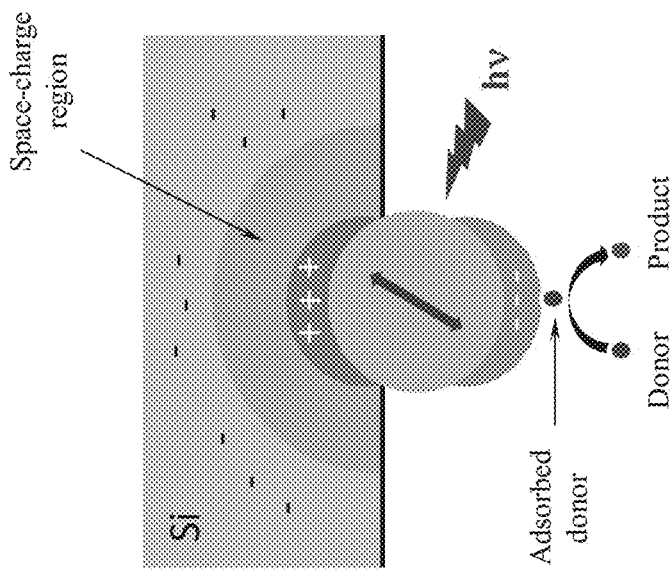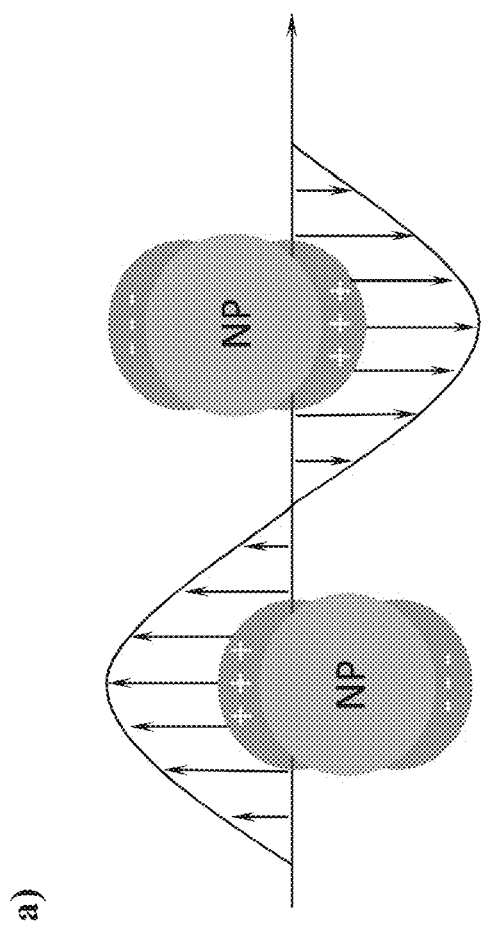
Fig. 8

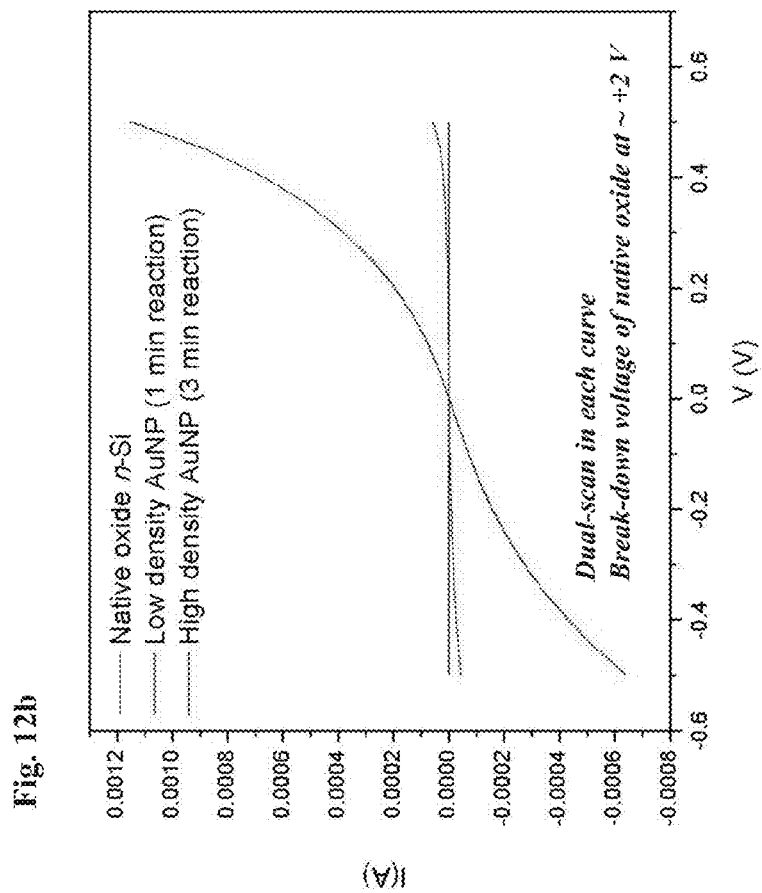
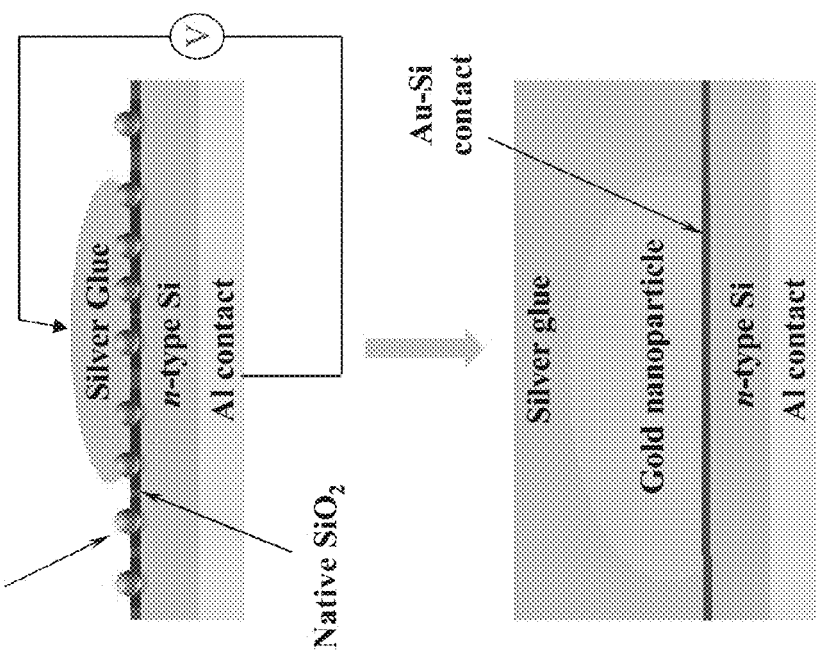
Fig. 12a
Fig. 12b

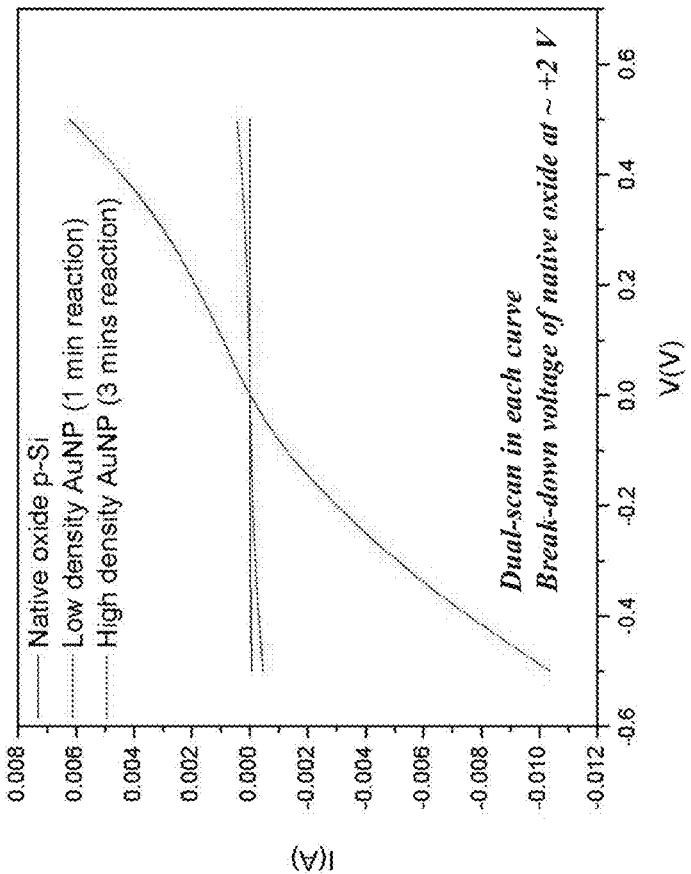
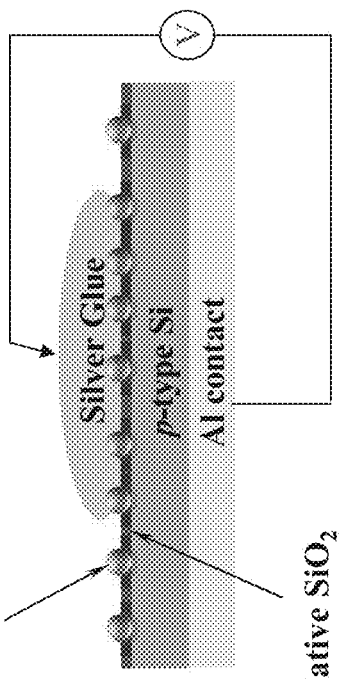
Fig. 13a
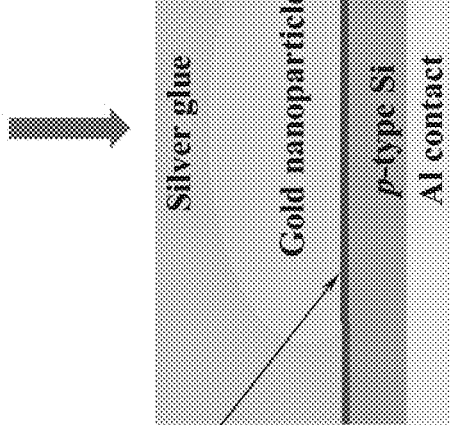
Fig. 13b

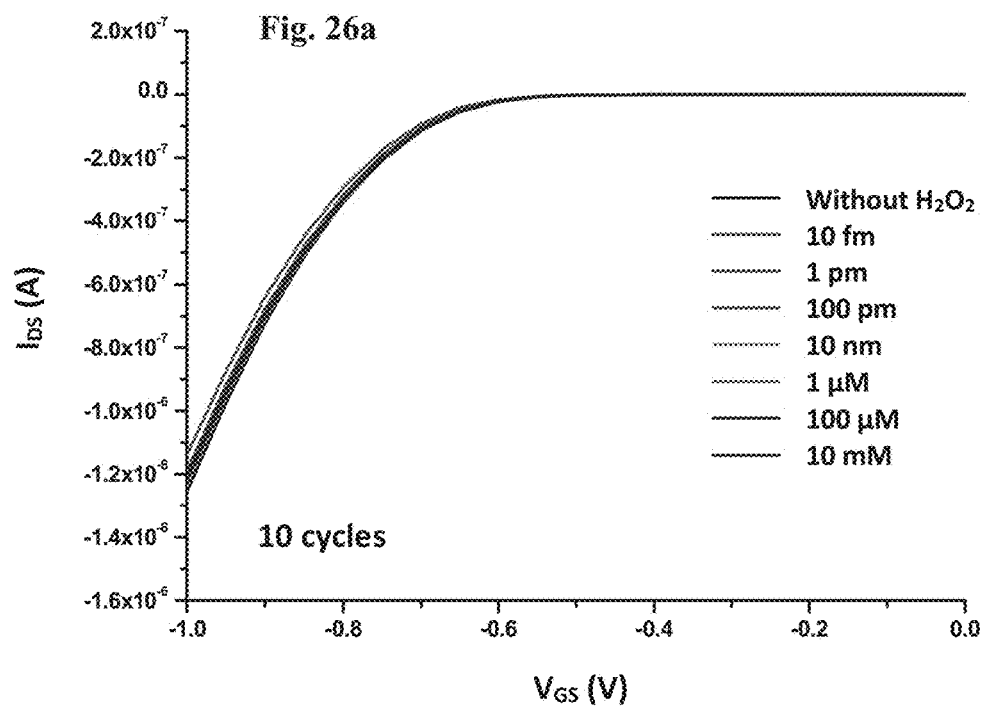
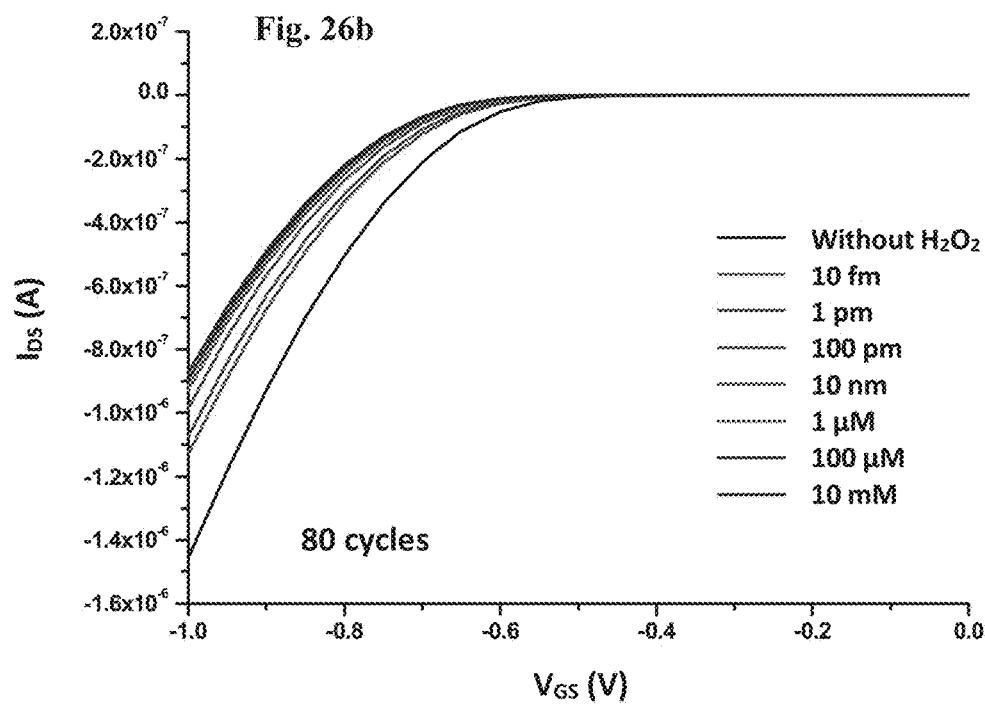

OPTOELECTRONIC PIXEL SENSOR

TECHNICAL FIELD

In general, the present application relates to the field of nanoelectronics. In particular, the present application relates to the nanoelectronic sensor pixel based on silicon nanowires decorated with optoelectronically active particles, and metal counter electrode structures.

BACKGROUND

Nanomaterials possess unique physical properties due to their confinement down to the nanometer scale in at least one dimension. Combination of nanomaterials and biological processes opens up new horizons for modern biotechnological applications, particularly for biosensing. Not only nanomaterials enable miniaturisation of devices, but also ensure their high sensitivity due to the significantly increased surface-to-volume ratio.

As nanomaterials in general, nanowires and their arrays in particular, confined down to the nanometer thickness, show many advantages over conventional wires, such as significantly increased signal-to-noise ratio, increased charge carrier transport and low detection limit. Therefore, the nanowires are now considered a new class of ultrasensitive electrochemical tools and electrochemical sensors.

However, since these sensor devices operate in ultralow current regimes and are in general very sensitive to various influences from side parameters, which generally decreases the stability and reliability of the sensor operation, special designs and array layouts are advised, which enable maximum control of the sensors performance. This includes a gate voltage control from front side via a stable electrochemical reference electrode system and from back side via a back gate contact. In addition a shift to the frequency domain for alternative sensor readout stabilisation aids more reliable performance in biosensor applications.

Silicon nanomaterials are a type of nanomaterials with attractive properties, including excellent semiconducting, mechanical, optical properties, favourable biocompatibility, surface tailorability, and are relatively compatible with conventional silicon technology. A silicon nanowire (hereinbelow, "SiNW") is defined as a "one-dimensional" silicon nanostructure exhibiting a length-to-diameter ratio of 1000 or more. The diameter of a regular SiNW is in order of manometers. At this scale, quantum mechanical laws become totally dominant, and SiNWs have many interesting properties that are not seen in larger objects and three-dimensional materials. Since quantum confinement of electrons in SiNWs to one dimension is predicted to be substantial only at diameters below 3 nm, the band structure is strongly modified for these nanowires having diameters of manometers. The band gap in SiNWs increases for smaller diameters and a direct band gap can be obtained for sufficiently small diameters. Silicon nanowires have been extensively explored for myriad applications ranging from electronics to biology (M. Zhang et al 2008).

A field-effect transistor (FET) is a semiconductor-based device with relatively low power consumption used for switching or signal amplification in electrical circuits. Widely used transistors are metal oxide semiconductor field-effect transistors (MOSFETs) having two highly doped domains (n- or p-type) separated by a p- or n-type domains, respectively, with p-n or n-p junctions at the interface enabling a tunnelling operation. Common elements for doping of silicon are boron (p-type) or arsenic/phosphoric (n-type).

The doped domains are connected to source (S) and drain (D) ohmic contacts. A metal gate is placed on top of the area between the S and D contacts, separated by a thin insulating oxide layer. Conductance of the transistor is controlled by an external field, for instance the gate field. By applying a positive or negative gate voltage at the gate, electrons are either attracted or repulsed at the semiconductor-oxide interface. Once the threshold voltage is reached, an inversion layer forms a conducting channel between the n- or p-type regions connected to the S and D contacts. Size of the formed channel depends on both, the external gate field and the selection of the materials. Applying an additional SD bias voltage enhances the charge carrier movement through the channel and narrows the channel at one certain end. Thus, conductance is altered, and electrons become attracted by the drain.

Ion-sensitive FETs (ISFETs) are similar to the common MOSFET, but the metal gate electrode is replaced with an electrolyte solution carrying analyte molecules and containing a reference electrode. The electrolyte solution is defined as a "liquid gate" which controls the current between the S and D contacts. The liquid gate electrode is separated from the channel by the gate insulator and/or an ionic "double layer" barrier, which is sensitive, for example to protons, and therefore, suitable for pH measurements. In general, binding reactions of charged analytes with corresponding ligand groups at the ISFET sensor surface cause a surface charge which leads to an additional surface potential. This change in surface potential is monitored and can be related to the number of adsorbed analyte molecules. Using different surfaces and surface functionalisation techniques, sensitivity to specific target analyte molecules can be achieved with this sensor. For sensing, it is important to include a reference electrode to control the solution potential and to apply the liquid gate voltage.

Conductance in ISFETs is strongly dependent on the charge density at the oxide-electrolyte interface. ISFETs are sensitive towards any electrical fields in general, and to charged molecules in particular. Depending on the point of zero charge of the surface and the pH of the electrolyte a respective surface charge is building up, the charging of the terminal surface groups behaves like a local gate potential. Therefore, it is possible to detect variations in the pH of the solution, i.e. taking or giving away protons at the functional interface is sensed. For the transfer characteristics of the devices, the source drain current ($I_{SD}$) is measured as a function of the applied gate voltage $V_G$. In a semi-logarithmic scale, the steepest slope of the curve $I_{SD}$ vs $V_G$ is defined as a sub-threshold swing with the threshold voltage $V_T$ at which the current is switched on due to the formation of an inversion layer at the insulator-semiconductor interface. At this point the FET switching can happen at maximum speed. By analysing this slope, which is constant over several orders of magnitude, curve shifts at a fixed current due to attached charged molecules can be determined ($\Delta V_T$).

Because of the possible (de)protonation of the surface oxide, pH measurements are usually applied to probe the device performances for potential application in biosensing. By changing pH, the surface potential is directly affected and influences the $V_T$. As a result, the curve of $I_{SD}$ vs $V_G$ shifts to lower or higher voltage values. Sensitivity of ISFETs is thus determined by the maximum possible shift because of a pH change, and defined by the Nernst limit at 300 K, as explained in detail by Tarasov in his PhD thesis *"Silicon Nanowire Field-effect Transistors for Sensing Applications"* (2012).

As most biomolecules display charges at their outer surface, ISFETs are equally sensitive to biomolecules such as proteins or DNA. Thus, their $I_{SD}$ vs $V_G$ curve shifts parallel to the $V_G$ X-axis when the charge density changes, and can be further analysed the same way as described for the aforementioned pH measurements.

Bavli et al (2012) showed a two-dimensional (planar) FET (used as a molecularly controlled semiconductor resistor), run in liquid environment, for the detection of different analytes on a lipid bilayer functionalized surface with a detection limit in the μg/ml range, which clearly indicates that this FET lacks low detection limits. SiNWs are integrated in field-effect transistors (FETs) to build sensor devices with strong signal amplification at low power consumption, which is advantageous for portable or implantable devices. One-dimensional FETs strongly benefit from an extreme surface area to volume ratio, which allows effective channel gating from even just a few adsorbed analyte molecules. SiNW-based FET sensing was described first by Cui et al in 2001 using vapour-liquid-solid (VLS) grown silicon nanowires (SiNWs) for pH sensing and detecting the binding of streptavidin protein on biotin-labelled wires. To date they demonstrated sensing of DNA/PNA hybridisation (Hahm and Lieber 2004), viruses down to single virus detection events (Patolsky et al 2004), using antibodies as receptors, multiplexed sensing (Patolsky et al 2006) and cell potentials (Jiang et al 2012).

SiNW-based FETs used for biosensing belong to the group of ISFETs and therefore operate in liquid medium. SiNWs compared to ISFETs offer higher surface-to-volume ratios for better sensitivity and small cross-sectional conduction pathways. Thus, they can overcome the detection limits of planar ISFETs. SiNW-based FETs have a conductance of 4-10 times higher than planar standard ISFETs of the same sizes due to their high surface-to-volume ratio and the efficient penetration of the gate field.

In biosensing applications of SiNW FETs, as in ISFETs, liquid also acts as a gate electrode and variations in the surface potential are converted to a conductance change in the channel. Actually, different from planar ISFETs, the one-dimensional SiNWs themselves are conduction channels, which are fully affected by the surface potential. Biological recognition events strongly alter the surface potential of the SiNWs even at low analyte concentrations. Charged biomolecules can locally act as liquid gate leading to resistivity changes, which (resistivity) is very sensitive to the biorecognition event. Due to signal amplification by the FET, the signal can be detected by significant jumps in the voltage at a fixed source drain current. Commonly, single-crystalline nanowires are with p- or n-type doping containing charge carriers that are attracted or repelled by the attaching charged biomolecules.

SiNWs can be combined with existing processing technology on silicon wafers to fabricate chips, which significantly reduces the cost of disposable chips. Many groups developed SiNW arrays in top-down fabrication to measure biorecognition events like protein detection using antibodies (Elnathan et al 2012) or hybridisation (G. Zhang et al 2008). In order to use these devices as biosensors, the silicon dioxide ($SiO_2$) surface of SiNWs should be functionalised with biorecognition elements in a controllable manner.

For all the different applications, interface engineering and chemical functionalisation of the transducer ($SiO_2$) surface are crucial for biosensor development to assure an excellent sensor performance. Requirements are a stable receptor attachment under varying conditions, while preserving the functionality of receptors at the same time. Additionally, binding strategies will enhance the receptor orientation towards the target in solution whereas blocking protocols try to avoid unspecific attachment to reduce background signals. The main focus here is on chemical functionalisation of silicon dioxide surfaces of SiNWs and evaluation of the receptor-analyte interactions with the immobilised receptors using optical and electrical sensing methods using the SiNW-based FET.

Real-time, label-free, portable, low-cost, flexible and reliable sensors with lab on chip systems are long-needed biomedical diagnostic devices, and they are still challenging. Further requirements to evaluate novel biosensors are their sensitivity to detect low levels of the analyte, selectivity to avoid false positive signals and a fast response time that allows for rapid diagnosis. In terms of fabrication, the integration into existing technologies and production, the versatility of application and the possibility to produce at low costs are crucial. Reversibility of the biosensor would allow for repeated measurements to improve comparability.

Integration of nanomaterials into biosensor's transducer is one of the possibilities to meet some of the above listed requirements especially in terms of miniaturisation and sensitivity due to their high surface-to-volume ratio and the confinement within the nanometer scale in at least one dimension which leads to changes in the physical properties. SiNW based FETs fulfil many of these requirements. The use of nanomaterials and the possible integration into Si wafer processing technology enables miniaturisation of devices at low costs. The immediate current jump upon physicochemical changes without need for analyte labelling meet the requirements for the modern biosensor of being real-time and label-free.

J.-H. Ahn et al (2014) described a SiNW FET with local side-gates and SiNW surface decorated with palladium nanoparticles for hydrogen detection. The drain current of their sensor reversibly responded to hydrogen concentration. A control experiment, which used the sensor with a bare SiNW without Pd nanoparticles, proved that the hydrogen-sensitivity is originated from the palladium nanoparticles decorating the SiNW surface. S.-W. Ryu et al (2010) discussed the SiNWs decorated with gold nanoparticles for use in a biosensor for label-free DNA detection with enhanced sensitivity. The electric current flow between a source and a drain electrode was measured in order to sense the immobilisation of tested oligonucleotides and their hybridisation with target oligonucleotides.

S. Yan et al (2010) demonstrated the fabrication method of the SiNWs decorated with gold nanoparticles. These SiNWs were directly fabricated into an electrode for detection of bovine serum albumin in solution without any pre-treatment. H. Huang et al (2014) described a method for producing a finely dispersed CuO nanoparticle electrocatalyst on a SiNW surface by combining metal-assisted chemical etching, electroless deposition, and thermal oxidation. They used the sensor based on the SiNWs decorated with CuO for sensing hydrogen peroxide.

To improve stability of the sensor arrays and ensure reproducibility of the readout, sensors of disclosed embodiments are fabricated in a parallel batch process on standard silicon wafers. To enable a control in bioassays, reference sensor structures such as temperature sensors, pH sensors and ionic strength sensors are added to the sensor chip. As discussed below, the design of the pixel array in a three-electrode configuration including a reference electrode and a counter electrode enables an additional operation of the optoelectronic sensor pixel in the frequency domain and helps to stabilize the electronic readout when recording very small DS current changes. Therefore this sensor can be additionally used for impedance spectroscopy applications. A combination of potentiometric and impedimetric readout enables a more reliable sensing of biomolecules with the potential to sense beyond the Debye screening of electrical charges in an electrolyte solution, which is usually the limiting factor in SiNW sensors with only potentiometric or conductometric readout.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

SUMMARY

In an embodiment, an electrical circuit element, defined as "optoelectronic pixel", comprises at least one silicon nanowire decorated with optoelectronically active particles and open for contact with a medium for sensing; a metal electrode open for contact with said medium and used for feeding a high-frequency sinusoidal stimulation in impedance measurements and for sensing properties of said medium; implanted source and drain electrodes connected to said silicon nanowire and leaving the gate area and parts of said electrode open for contact with said medium; electrical metal contacts for connecting said pixel to an electrical circuit; and a reference electrode open for contact with said medium for creating a three-electrode-cell system and providing a constant gate potential in the circuit.

The pixel of an embodiment may further comprise a backgate contact for the full electrostatic control of the pixel sensor and for stabilising the electronic recording in electrolyte solutions. The metal electrode of the optoelectronic pixel can be a noble metal counter electrode or a temperature sensor, or both a counter electrode and temperature sensor, simultaneously. The reference electrode can be an Ag/AgCl reference-cell electrode or a similar reference electrode system.

The optoelectronically active particles of an embodiment are metal nanoparticles, metal oxide nanostructures, or a combination thereof. The metal nanoparticles can be made of Ag, Cu, Au, Al, Pd, Pt, Ni, Co, Pb, Ti, Fe or Cr, while the metal oxide nanostructures can be made of CuO, $ZnO_2$, $In_2O_3$, $SnO_2$, IZO, GZO, ITO, IGZO, IZTO or ZTO. The surface of the optoelectronically active particles can be functionalised with receptor (capture) molecules capable of binding to target (analyte) molecules. The pixel of an embodiment can further comprise an excitation light source, such as a laser diode or a light-emitting diode (LED), for irradiating the optoelectronically active particles, thereby creating localised surface plasmon resonance (LSPR) on said particles.

In addition, an embodiment provides an optoelectronic sensor and wearable-patch sensor based on the array of the optoelectronic pixels, and the readout methods for the sensors.

BRIEF DESCRIPTION OF THE DRAWINGS

Embodiments of the present application will be understood and appreciated more fully from the following detailed description taken in conjunction with the appended figures.

FIGS. 1(a)-(c) schematically show the layout of an 8-channel SiNW ISFET sensor chip with a triple functionality readout embedded on the chip.

FIGS. 1(d)-(e) show the optical microscopy images of an 8-channel SiNW ISFET sensor chip completely fabricated at the inventor's facility.

FIG. 4 schematically shows the optoelectronic pixel of an embodiment.

FIG. 6 schematically shows a mixed analogue/digital amplifier circuit comprising an array of the optoelectronic pixels on a sensor chip.

FIG. 8(a) illustrates the LSPR phenomenon based on the collective oscillation of metal free electrons in the electron cloud in phase while varying an electrical field of incident light.

FIG. 8(b) schematically shows the metal-silicon Schottky junction resulting from the contact of the metal with intrinsically doped silicon.

FIG. 12(a) schematically shows the test system for n-type silicon decorated with gold nanoparticles in a Silver Glue conductive paste.

FIG. 12(b) shows the results of electrical scanning of the system shown in FIG. 12(a).

FIG. 13(a) schematically shows the test system for p-type silicon decorated with gold nanoparticles in a Silver Glue conductive paste.

FIG. 13(b) shows the results of electrical scanning of the system shown in FIG. 13(a).

FIG. 26 shows the measurements of $H_2O_2$ at different concentrations conducted with the sensor pixel decorated with ZnO nanoclusters in (a) 10 cycles of the ALD process, and (b) 80 cycles of the ALD process.

DETAILED DESCRIPTION

Figure 1H:
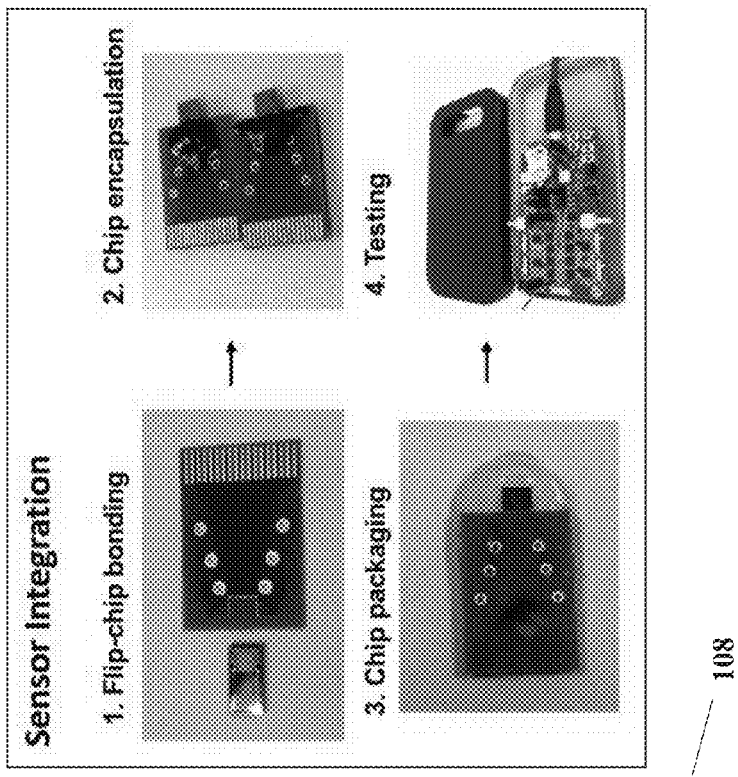
FIG. 1(h) demonstrates the steps of the sensor integration process.

Some disclosed embodiments provide a sensor pixel incorporating top-down fabricated silicon-nanowires (SiNWs) decorated with optoelectronically active particles, the pixel array and a nanoelectronic sensor chip based on this array. The distinguishing feature of the present sensor pixel is that 1) silicon nanowires (SiNWs) are decorated with optoelectronically active particles, and 2) the transistor contains integrated additional electrodes for additional sensing capabilities.

The "optoelectronically active particles" (herein, OAPs) are the metal or metal oxide particles decorating the SiNW and significantly increasing the drain-source electrical current, when optically excited with light. In a specific embodiment, the OAPs are metal nanoparticles, for example, made of Ag, Cu, Au, Al, Pd, Pt, Ni, Co, Pb, Ti, Fe, Cr. In another specific embodiment, the OAPs are metal oxide nanostructures, such as nanoparticles, nanoclusters, nanorods or nanoflowers. These metal oxide nanostructures can be crystalline or amorphous and can be made, for example, from copper oxide (CuO), zinc oxide ($ZnO_2$), indium oxide ($In_2O_3$), tin oxide ($SnO_2$), indium zinc oxide (IZO), gallium zinc oxide (GZO), indium tin oxide (ITO), indium gallium zinc oxide (IGZO), indium zinc tin oxide (IZTO) or zinc tin oxide (ZTO). In still another specific embodiment, the OAPs are combinations of the metal nanoparticles with the metal oxide nanostructures.

There are two main methods to fabricate single-crystalline SiNWs: bottom-up and top-down growth of the nanowire. In the bottom-up approach, single-crystalline SiNWs are grown with vapour-liquid-solid growth method (VLS). This approach is technologically much easier, but a scale up for industrial fabrication and mass production is not feasible. Although the bottom-up method produces very thin and sensitive wires in the range of 10 nm, it has a low reproducibility. In fact, bottom-up approach has thus far prevented the commercialisation of such nanowire sensors mainly due its incompatibility with reproducible, high-volume manufacturing. In contrast, various top-down methods entail a high level of non-standard processing complexity and high process variation.

The SiNW pixel arrays of some embodiments are therefore fabricated using a top-down method, which has the advantage of producing more robust transistors. In addition, this approach addresses the problems of placement, integration, and reproducibility encountered with bottom-up materials. The modified top-down method, which was developed by the present inventors and described in Vu et al (2009 and 2010), combines wafer-scale nanoimprint lithography techniques defining nanowires from thin single crystalline silicon layers, reactive ion etching and further etching with tetra methyl ammonium hydroxide. After nanowire array fabrication, source and drain are doped by ion implantation to form electrode contacts, gate oxide is grown to create the gate dielectric layer, metal contacts are defined, and finally everything except the wire regions is passivated for sensor use in liquids.

The advantages of the top-down devices compared to those implementing bottom-up grown nanowires are the precise definition of the nanowire arrays on certain areas and the predetermined number of the nanowires on one device, which significantly increases the reproducibility.

The "open gate area" of the SiNW ISFET is defined as an area between the source and drain contacts of the transistor, which is directly exposed to a conductive medium, such as liquid or gas, capable of conducting electric current. An example of the conductive liquid is an electrolyte saline solution or buffer. In this case, instead of the fixed gate voltage, which is normally applied to a gate electrode, a reference potential is applied to the electrolyte-semiconductor system, via a reference electrode that is contacting the electrolyte. As a result, in the absence of the physical gate, the electrolyte itself becomes an open gate of the transistor.

FIGS. 1(a)-(c) show the layout of the 8-channel SiNW ISFET chip with multiple readout functionality embedded on the chip. This chip served as a prototype for the sensor pixel chip of an embodiment. It also consists of contact leads arranged in different arrays. At one end of the chip, silicon nanowires (100) are placed between source (101) and drain (102) contact leads.

The distinguishing feature of an embodiment is that the SiNWs (100) of the sensor chip are decorated with OAPs. Through the common source (101) and eight individual drain contact leads (102), the different SiNWs can be addressed. The chip further contains a reference electrode (103), which is used to apply a stable liquid potential for gate bias. In addition, the chip contains a common metal electrode (104), which can be used as an input for high-frequency AC sinusoidal stimulation in the impedance measurement, a counter electrode or a temperature sensor microelement. In addition, there are back gate contacts (105) to connect the back gate of the transistor (i.e. the silicon handle wafer below the buried oxide layer) to the circuit in order to tune the working point of the front gate and keep the potential of the bulk silicon stable during measurements. Further, an optional microfluidic flow cell (106) for analyte delivery to the chip may also be added to the chip.

The chip can be scalable-manufactured on 2-20 inch silicon wafers using the top-down method, as mentioned above. The 4-inch silicon wafer contains, for instance, 500 chips with 300 chips in the centre of the wafer. The fabricated chips have a size of 2.5×5 mm which can be varied dependent on a particular application. The reference electrode (103) is integrated on the chip in an additional metallization step of the top-down fabrication. There can be one, two or more reference electrode leads (103) printed on the chip. They can be connected together or used separately. The reference electrode leads (103) are printed on the chip as Ag electrode leads and then chlorinated to obtain the Ag/AgCl reference electrodes. The Ag/AgCl system can only be regarded as a pseudo-reference system, since it is very dependent on chloride concentration. However, in combination with an ionic-strength sensor in the pixel array, this side effect can be avoided.

In a particular embodiment, the metal electrode (104) is a noble metal electrode, such as platinum counter electrode. In another particular embodiment, the metal electrode (104) is a temperature sensor. In yet further embodiment, the metal electrode (104) is used for the high-frequency AC sinusoidal stimulation in the impedance measurement of the sensor. In a specific embodiment, the metal electrode (104) is used as a counter electrode and temperature sensor, simultaneously. This functionality requires a specific switch being installed in the electronic readout module in order to select the operational mode of the metal electrode (104), either as a counter electrode or as a temperature sensor during the measurements. This enables a stable readout and cancels out temperature effects during recordings.

In another embodiment, the microfluidic flow cell (106) comprises a microfluidic chamber having inlet and outlet for a fluid circulating through the chip and delivering the analyte to the SiNWs (100) in a continuous flow. The SiNW ISFET can operate with both back gate and front gate. The back gate electrodes (105) are used to tune the working point of the front gate. They also have a function of keeping the potential of the bulk silicon stable during experiments.

The lowly-doped SiNWs (100) can be of n-type or p-type, or can be configured as tunnelling silicon nanowire devices (drain n-doped and source p-doped or drain p-doped and source n-doped), and the SiNW ISFET can be operated as p-type transistor or n-type transistor depending on the doping and on the applied voltages to the gate. Generally, in contrast to back-gate operation, the electric signals of the front-gate operations were stable and reliable. A subthreshold slope of 90 mV/decade indicated that a high quality front-gate oxide was achieved in the fabrication process, which can enhance the sensitivity of the SiNWs devices.

FIG. 1(d)-(e) show optical microscopy images of 8-channel SiNW ISFET sensor chip described above and used in the preliminary experiments. As seen in these figures, contacts of the reference electrode (103) are connected via cutting lines (110) of the chip for a wafer-scale chlorination of the Ag/AgCl electrode system.

Figure 1G:
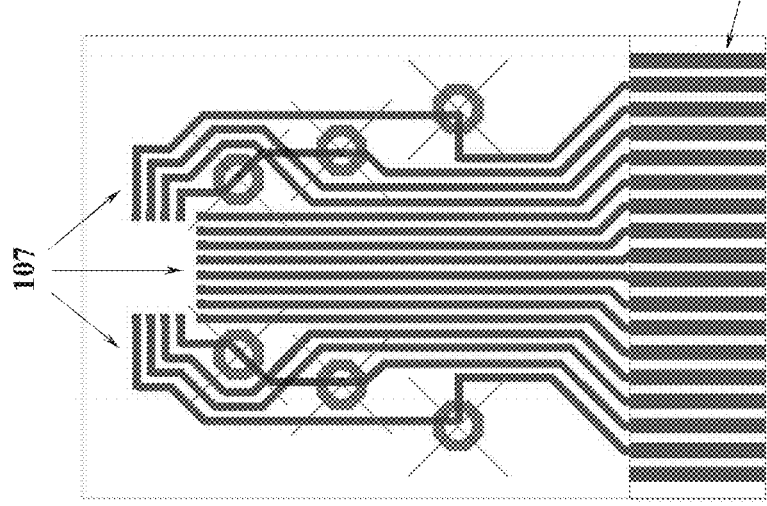
FIGS. 1(f)-(g) shows the actual 8-channel SiNW ISFET sensor chip of an embodiment.
Figure 1F:
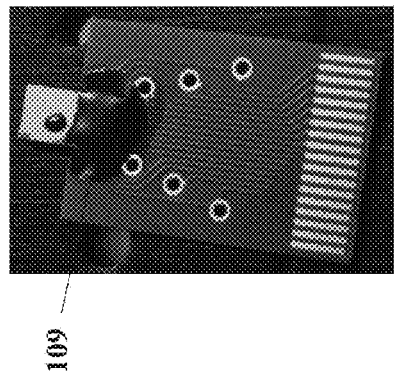

FIGS. 1(f)-(g) demonstrate the actual 8-channel SiNW ISFET sensor chip completely fabricated at the inventor's facility. Contact pads (107) are available for flip-chip bonding of the chip, while contacts (108) are used for connecting the chip to a circuit via a flat flexible connector (FCC). A sensor-integration process, which is shown in FIG. 1(h), comprises the steps of: 1) flip-chip bonding, 2) chip encapsulation, 3) chip packaging, and 4) chip testing. As an example, the 2.5 mm×5 mm chips were cut from the fully-processed silicon wafer and then cleaned with acetone and isopropanol in order to remove the protection resist. Due to the mechanical properties of the SiNW, the cleaning steps needed to avoid strong mechanic treatment like ultrasound or mechanical manipulation.

The electrical contact between the bond pads on the chips and the carriers was formed by printing of a two-component conductive silver glue (109), for example Epo-Tek H20E-PFC, (PolytecGmbH, Waldbronn, Germany), on the contact areas of the carrier using a screen printer, such as SP-002 (Essemtec AG, Aesch, Switzerland). Then the chips were mounted to the back side of the printed circuit board carriers (WI-KA GmbH, Baesweiler, Germany) by flip-chipping using a precise X-Y positioning system, such as Fineplacer 96 (Finetech GmbH & Co. KG, Berlin, Germany). The glue was cured at 150° C. for one hour. Followed by application of a two component under fill epoxy, such as Epo-Tek U300, Polytec, or epoxy resin, such as Epo-Tek 302-3M, Polytec, around the chip. Due to its viscous properties, the epoxy was dragged between the chip and the carrier, thus insulating everything but the bond contacts electrically. The epoxy was then cured at 150° C. for 1 hour. Finally, a small glass ring was glued on the carrier to form an electrolyte reservoir for initial testing of the sensors.

In a particular embodiment, the SiNWs (100) are decorated with OAPs, selected from metal nanoparticles, such as Ag, Cu, Au, Al, Pd, Pt, Ni, Co, Pb, Ti, Fe, Cr, or from metal oxide nanostructures (nanoparticles, nanoclusters, nanorods or nanoflowers), such as CuO, $ZnO_2$, $In_2O_3$, $SnO_2$, IZO, GZO, ITO, IGZO, IZTO or ZTO. In still another specific embodiment, the SiNWs (100) are decorated with combinations of different OAPs, for example, metal nanoparticles with metal oxide nanoclusters.

The SiNWs can be decorated with OAPs using either an electroless growing method or a sputtering technique. The "electroless" growing of OAPs on a SiNW surface is a process that allows the OAPs to grow directly and selectively on silicon without applying any electrical field, as will be detailed in the Examples. Most of the SiNWs of an embodiment were decorated with OAPs using the electroless growing approach. The deposition techniques can be of either physical or chemical nature, which involves the growth of OAPs' metal onto a silicon wafer. In the most simple approach already prepared OAPs can be deposited to the surface by physical adsorption.

Figure 2A:
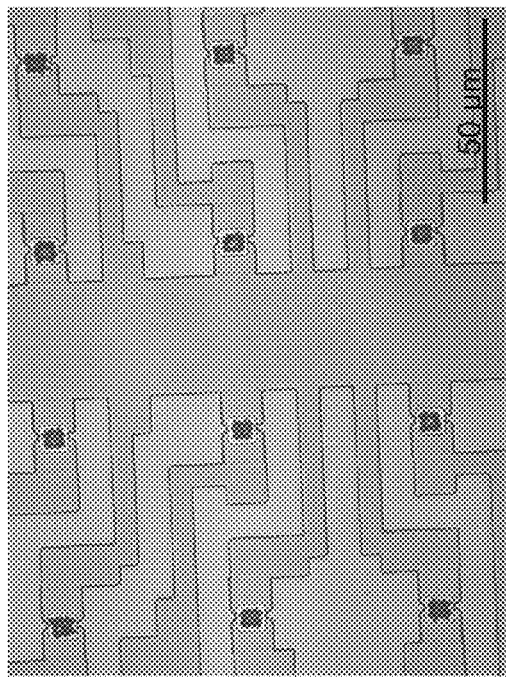
FIG. 2(a) shows the microscope image of the bare ISFET array of an embodiment.
Figure 2B:
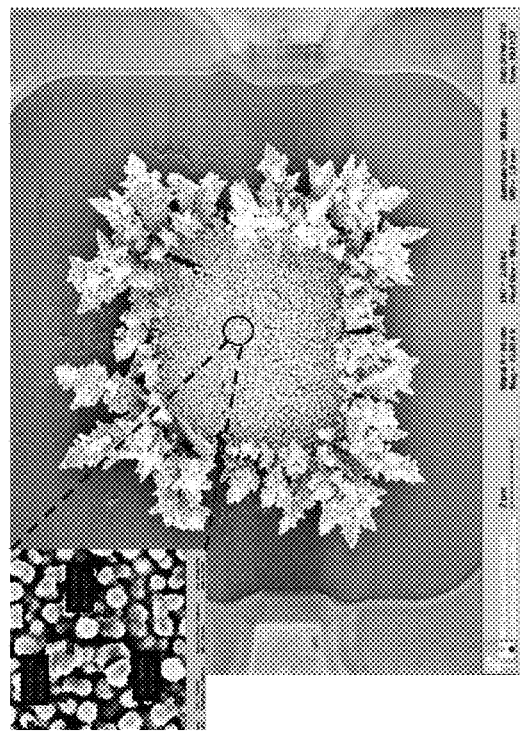
FIG. 2(b) shows the microscope image of the ISFET array of an embodiment decorated with gold nanoparticles using the electroless method.
Figure 2C:
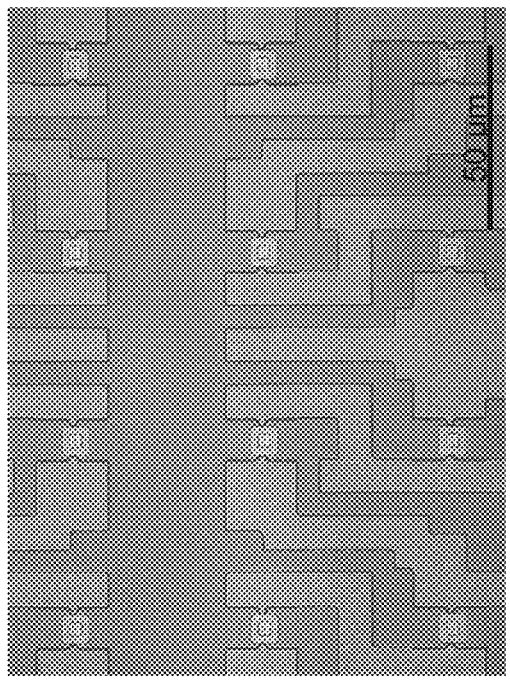
FIG. 2(c) shows the close-up image of FIG. 2(b).
Figure 2D:
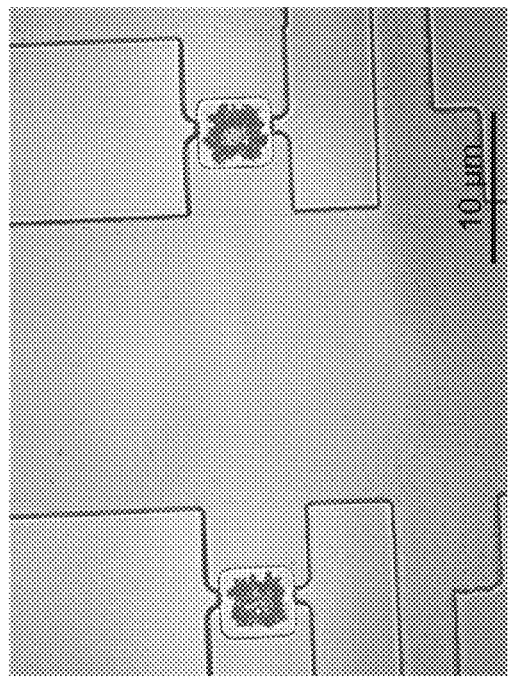
FIG. 2(d) shows the SEM image of one-gate structure from an ISFET array of an embodiment decorated with gold nanoparticles. Inset shows a close-up image of the gold nanoparticles.
Figure 3A:
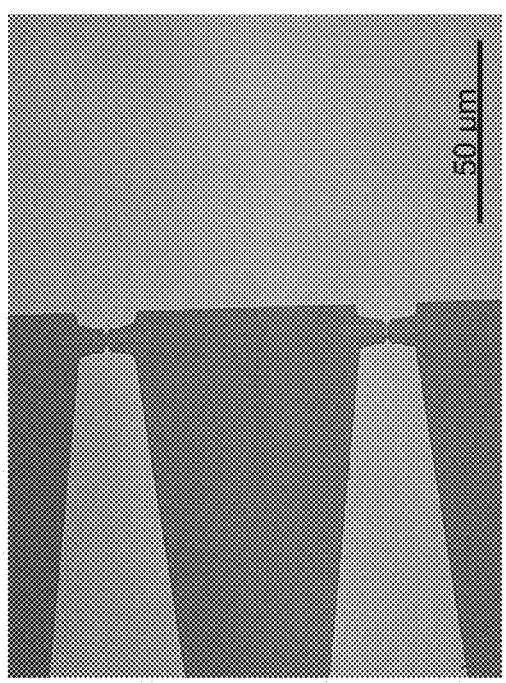
FIGS. 3(a)-(b) shows the microscope image of the SiNWs before and after the decoration process, respectively.
Figure 3B:
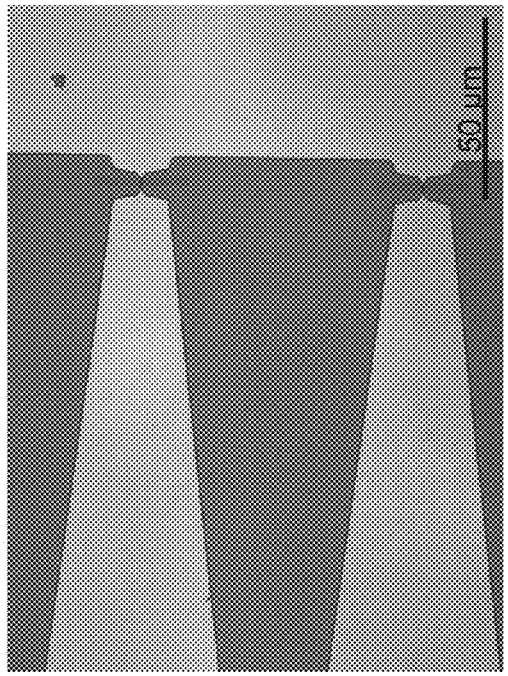
Figure 3C:
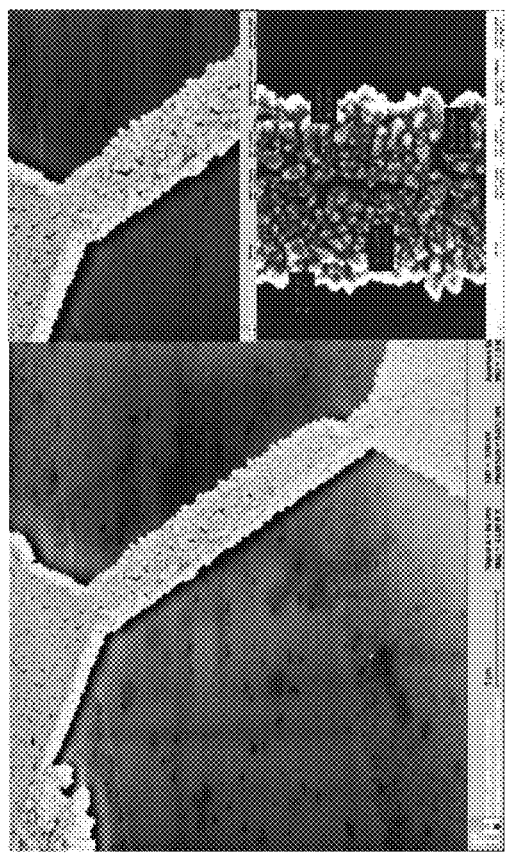
FIG. 3(c) shows the close-up and SEM images of the same SiNW decorated with gold nanoparticles.

FIG. 2(a) shows the microscope image of the ISFET array prior to decoration with gold nanoparticles, while FIG. 2(b) shows the microscope image of the ISFET array decorated with gold nanoparticles using the electroless method. FIG. 2(c) shows the close-up image of FIG. 2(b), and FIG. 2(d) shows the SEM image of silicon decorated with gold nanoparticles. Further, FIGS. 3(a)-(b) shows the microscope image of the SiNWs before and after the decoration process, respectively, while FIG. 3(c) shows the close-up and SEM images of the same SiNW decorated with gold nanoparticles.

As defined herein, an "optoelectronic pixel", shown in FIG. 4, is an electrical circuit element comprising:
one or more silicon nanowires (201) decorated with optoelectronically active particles and open for contact with a medium, such as an ionic liquid or gas, for sensing;
a metal electrode (205) open for contact with said medium for feeding the high-frequency sinusoidal AC stimulation in impedance measurements and for sensing properties of said medium;
implanted source and drain electrodes (202) connected to said silicon nanowires (201) and leaving the gate area (206) and parts of said electrode (205) open for contact with said medium;
electrical metal contacts (203) for connecting said pixel to an electrical circuit; and
a reference electrode (204) open for contact with said medium for creating a three-electrode-cell system and providing a constant potential in the circuit.

In another embodiment, the optoelectronic pixel further comprises an excitation light source (216), such as a laser diode or LED, for irradiating said optoelectronically active particles and creating plasmon resonance on their surface.

In a particular embodiment, the silicon nanowires (201) are lowly-doped, etched from the top silicon layer of prime-quality silicon-on-insulator (SOI) wafer, which allows high carrier mobility, thereby improving performance. The source and drain electrodes (202) are highly doped, in order to reduce feed line resistance, and etched from the same top silicon layer of the SOI wafer in the same process step. The contact leads material is highly-doped silicon, a highly-doped polysilicon layer, a metal layer or preferably, a silicide, such as CoSi, PtSi or TiSi.

In a specific embodiment, the metal electrode (205) is a noble metal electrode, such as platinum counter electrode, which can also be used as a temperature sensor. In a further specific embodiment, the metal electrode (205) is used as a counter electrode and temperature sensor, simultaneously. In yet further embodiment, the metal electrode (205) is used for the high-frequency AC sinusoidal stimulation for the impedance measurements of the sensor. In a particular embodiment, the reference electrode (204) is an Ag/AgCl reference-cell electrode. The metal electrode (205) is chosen according to an established technology and an assembly line at a particular clean room fabrication facility. The metal electrode (205), as well as the reference electrode (204), is not passivated since they both should be in direct contact with the tested medium. Therefore, there is an opening (214), which is made in the passivation layer (215), for leaving the sensing elements of the pixel open to the medium. As will be shown below, the actual sensor will include many pixels in an array, one common metal electrode and one common reference electrode for all the pixels.

The electrical metal contacts (203) contacting the silicon source and drain connect the pixel to the electrical circuit and allow the electric current to flow in the system. One layer of these contacts is made of aluminium or silicide, such as CoSi, PtSi or TiSi, in order to form a surface alloy with the silicon, thereby providing an electrical ohmic contact to the silicon. The term "ohmic" contact means that it has a straight line in the current-voltage characteristics. These ohmic metal contacts (203) are made of metal or metal stacks, such as Al, Al/Ti/Au or similar. Another layer of these contacts is not contacting silicon and used to promote adhesion to the underlying layers of $SiO_2$ and $Si_3N_4$, which are used for isolation. Cr and Ti are examples of such adhesion promoters. The Cr or Ti layers of the metal stack is, for example, of 5-10 nm thickness, while the second metal layer, such as Au, Pt and Cu, is of 100-400 nm thickness. In order to limit the capacitive coupling of the source and drain contact leads and to avoid leakage current into the signal of the sensor, the source and drain contact leads are further covered by a thick layer of insulators.

Figure 5A:
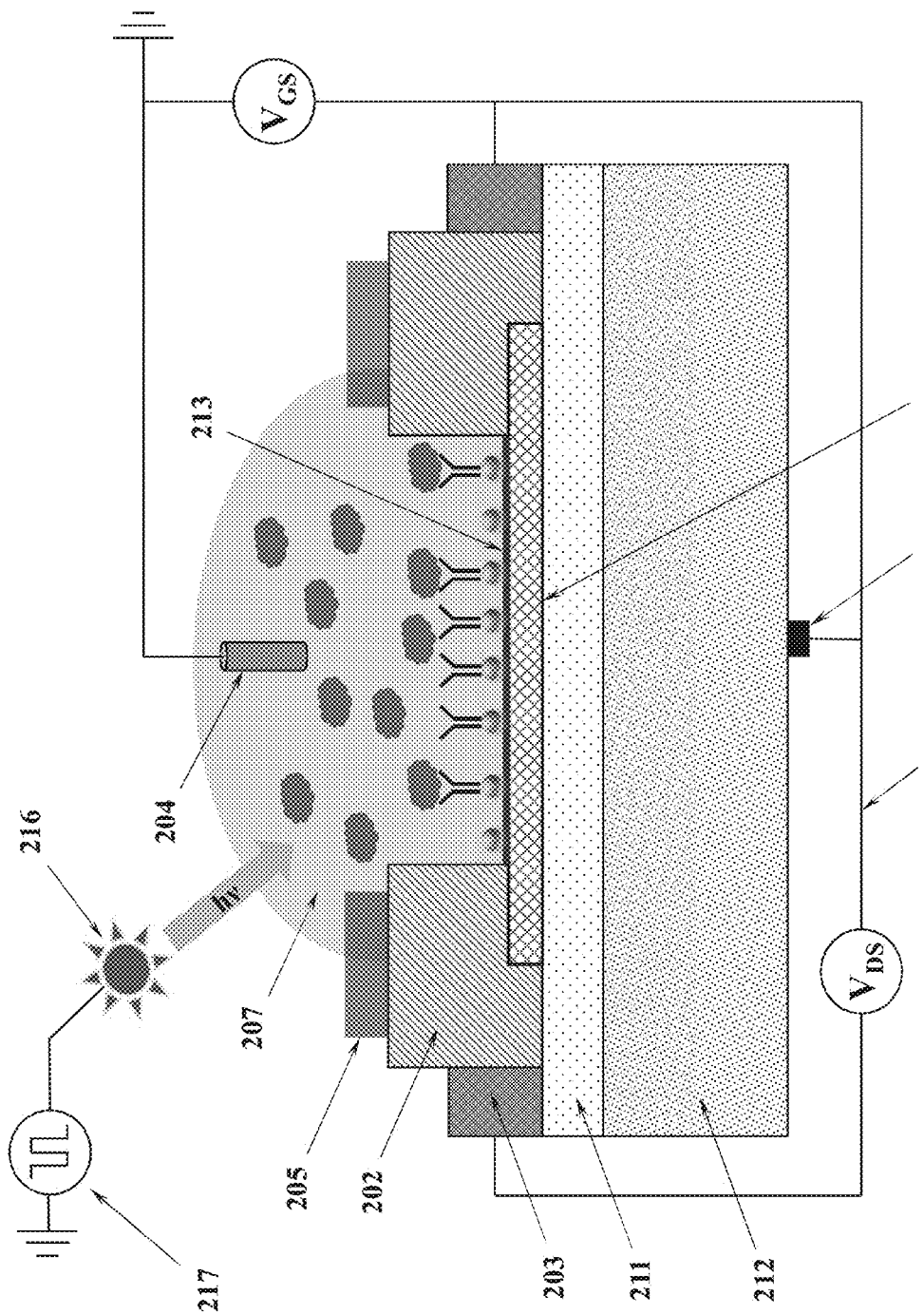
FIG. 5(a) schematically shows the cross-section of the optoelectronic pixel sensing a liquid sample, which contains analyte molecules.

FIG. 5(a) shows the cross-section of the pixel sensing a liquid sample (207), which contains analyte molecules. The pixel is connected to the circuit (210). As noted above, the pixel is manufactured using the modified top-down approach from SOI wafer substrates (212) with about 40-60 nm in thickness of the top silicon layer and a silicon buried oxide (BOX) (211) of approximately 100-400 nm thickness, which acts as an insulator layer. At room temperature and under the assumption that no fixed oxide charges exist, the SiNW (201) is fully depleted of charge carriers in thermal equilibrium. The pixel may further comprise a back gate (208) at the bottom of the handle wafer substrate (212). The back gate is used for tuning the threshold voltage, since the body of the pixel influences that voltage. The excitation light source (216) is used to irradiate said optoelectronically active particles and create plasmon resonance on their surface. In a specific embodiment, the light source is a laser diode. In case the OAPs are gold nanoparticles, the light source is a laser diode with the 905 nm excitation wavelength. The light source (216) is connected to the function generator (217), which modulates the light source by feeding a sinusoidal waveform signal to it.

The open gate formed by liquid or gas medium (207) effectively controls the charge flow in the SiNW channel. In the gate area (206) (from FIG. 4), the SiNW (201), which is placed between the source and drain electrodes (202), is coated with a gate oxide (213) layer and then decorated with OAPs. The light excitation source (216), such as a photo diode or a laser diode, is placed on top of the pixel to irradiate the OAPs and create plasmon resonance on their surface. The SiNW acts as a channel to allow the flow of charge carriers from one electrode to another. This is particularly useful for DC sensing.

The gate oxide, also called the gate capacitor or dielectric (213), is a thin layer of oxide or nitride dielectric material, such as $SiO_2$, $Al_2O_3$, $TaO_2$, $HfO_2$, $TiO_2$, $ZrO_2$, TiN, $Si_3N_4$, or similar. It is grown on top of the silicon substrate between source and drain, protecting the surface of the SiNW from an electrolyte solution, acting as a capacitor for the field effect and providing good pH sensitivity. In case of $TaO_2$ or $Al_2O_3$, it is an almost ideal pH sensor. The OAPs are further grown or deposited on top of the gate oxide.

In case of $SiO_2$, the gate oxide (213) has a preferable thickness of 6-8 nm and isolates the SiNW from an electrolyte. The BOX layer (211) of approximately 100-400 nm thickness separates the SiNW from the handle wafer substrate (212) of about 500 μm thickness. Hence, the concentration of charge carriers in the nanowire can be controlled by an electric potential that can either be applied from the top through the thin oxide layer (213) or from the bottom through the thick BOX layer (211). The first gate is called "front gate" (FG), while the second is called "back gate" (BG). Like in any SOI fully-depleted device with a very thin top silicon layer, both gates are strongly coupled electrostatically. This indicates that the back-gate potential affects the front-gate characteristics and vice versa. Thus, depending on application purposes, the gate surface of the pixels can be further modified by depositing other materials on the oxide layer, such as $Si_3N_4$, $SiO_2$ or similar listed above, for pH sensors, monolayer of polymer for biomolecular binding, or high-k materials to enhance the electronic coupling with biology systems.

Figure 5B:
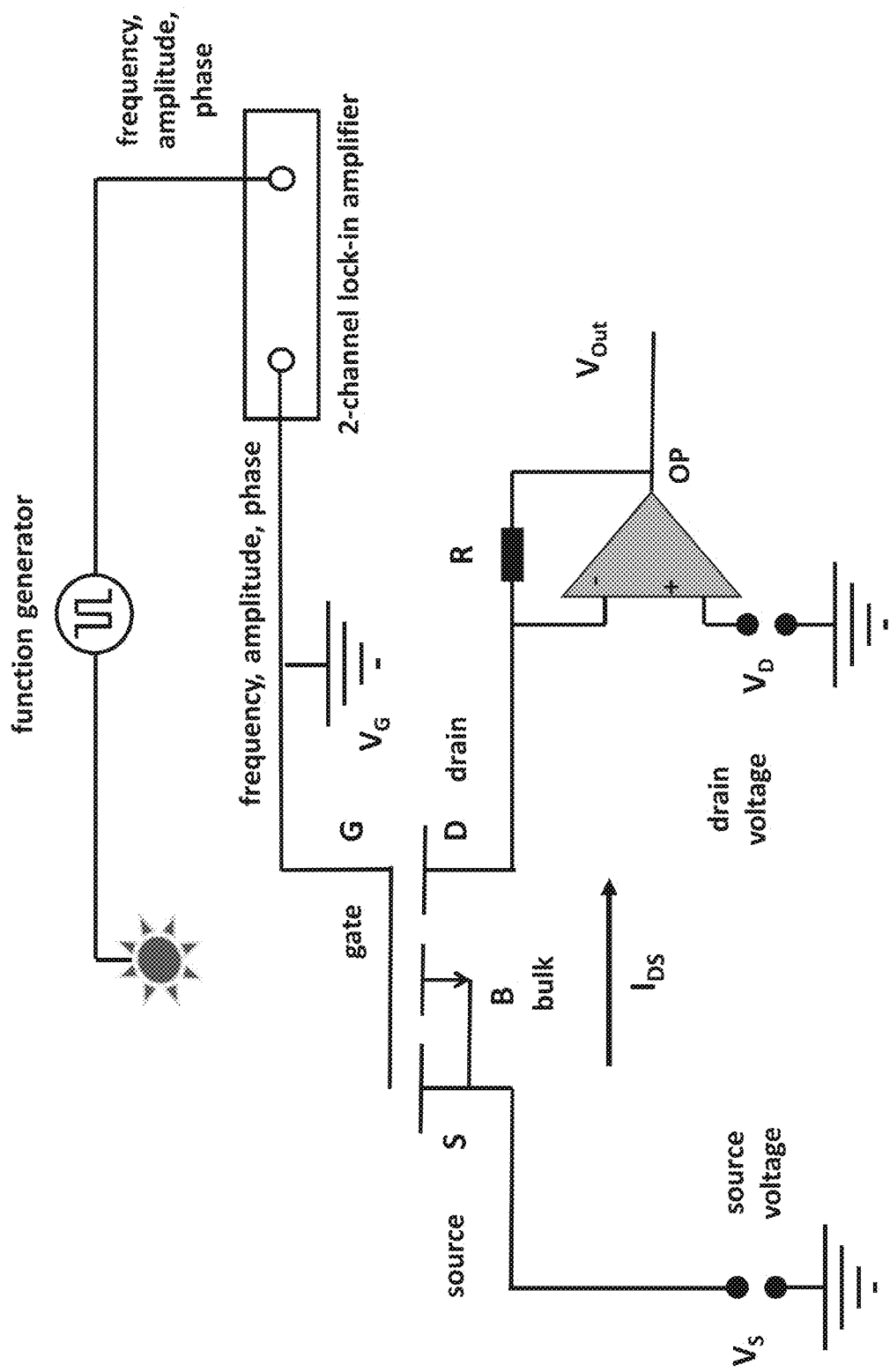
FIG. 5(b) showing an accumulation mode field-effect transistor with light excitation in a two-channels transimpedance amplifier circuit having the electrolyte gate at ground potential.

Reference is now made to FIG. 5(b) showing an accumulation mode field-effect transistor with light excitation in a transimpedance amplifier circuit, wherein the transimpedance amplifier includes an operational amplifier (OP) and a resistor. The transistor is brought into its working point by applying drain-source $V_{DS}$ and gate-source $V_{GS}$ voltage. The transistor is configured such that the gate contact is at ground potential. Therefore the source voltage $V_S$ and the drain voltage $V_D$ are applied. These can be converted by: $V_{GS}=-V_S$ and $V_{DS}=V_D-V_S$. Thus, the voltage sources $V_S$ and $V_D$ (while $V_G$ is at ground) are linked together to result in voltage differences $V_{GS}$ and $V_{DS}$, which are usually plotted for the transfer characteristics. In the transistor working point, the drain-source current $I_{DS}$ is flowing through the device. This is converted into an output voltage $V_{out}$ by the operational amplifier (OP), while the amplification factor F is set by the feedback resistor R. The OP is connected at its inverting amplifier input (−). The total amplification of this first amplifier stage is given by the product of the transistor's transconductance ($g_m$) (which will be discussed below) in the respective working point times the feedback resistor: $F=g_m \times R$.

The light excitation circuit of the above transistor includes a light source, a function generator modulating the light source, and a 2-channel lock-in amplifier. As will be explained below, the light frequency is modulated with the function generator to match the AC impedance frequency of the SiNW, thereby creating the optoelectronic resonance in the system.

The SiNWs produced by the top-down process are usually treated as long-channel ISFETs of nano size. The sensing mechanism of these SiNW ISFETs is based on the accumulation of charged molecules near the SiNW surface, which leads to a surface potential shift. The transistor then responds to changes in the surface potential with a threshold voltage shift. While in MOSFETs, the metallic gate is in direct contact with the dielectric over the channel, in the ISFETs, the gate (reference) electrode is a distance away from the dielectric, with an intervening sample fluid. Changes at the dielectric-solution interface alter the surface potential, which acts as an additional gate voltage. The gate voltage $V_{GS}$ is applied using a reference electrode to set the operating point of the device, and the conductance of the channel is measured by applying a drain-to-source voltage $V_{DS}$. Thus, the gate voltage actually modulates the current between the source and the drain.

FIG. 6 shows an array of the optoelectronic pixels (10) on a sensor chip. Each pixel comprises one silicon nanowire (11) decorated with OAPs and exposed to liquid or gas medium for sensing, an excitation light source (not shown), the implanted source and drain (13) and their contact leads (14) connecting this SiNW to the circuit, and one common metal electrode (12) for feeding the AC sinusoidal stimulation and for conducting sensing or testing operations. A reference electrode (not shown) to set the DC bias voltage $V_G$ in the electrolyte is placed outside. All the pixels in the array operate synchronously having the same transfer characteristics. Therefore, it is essential to set all the gate contacts at a common ground potential (which is the reference electrode potential) in order to operate all the pixels in the array at the same time.

Figure 7:
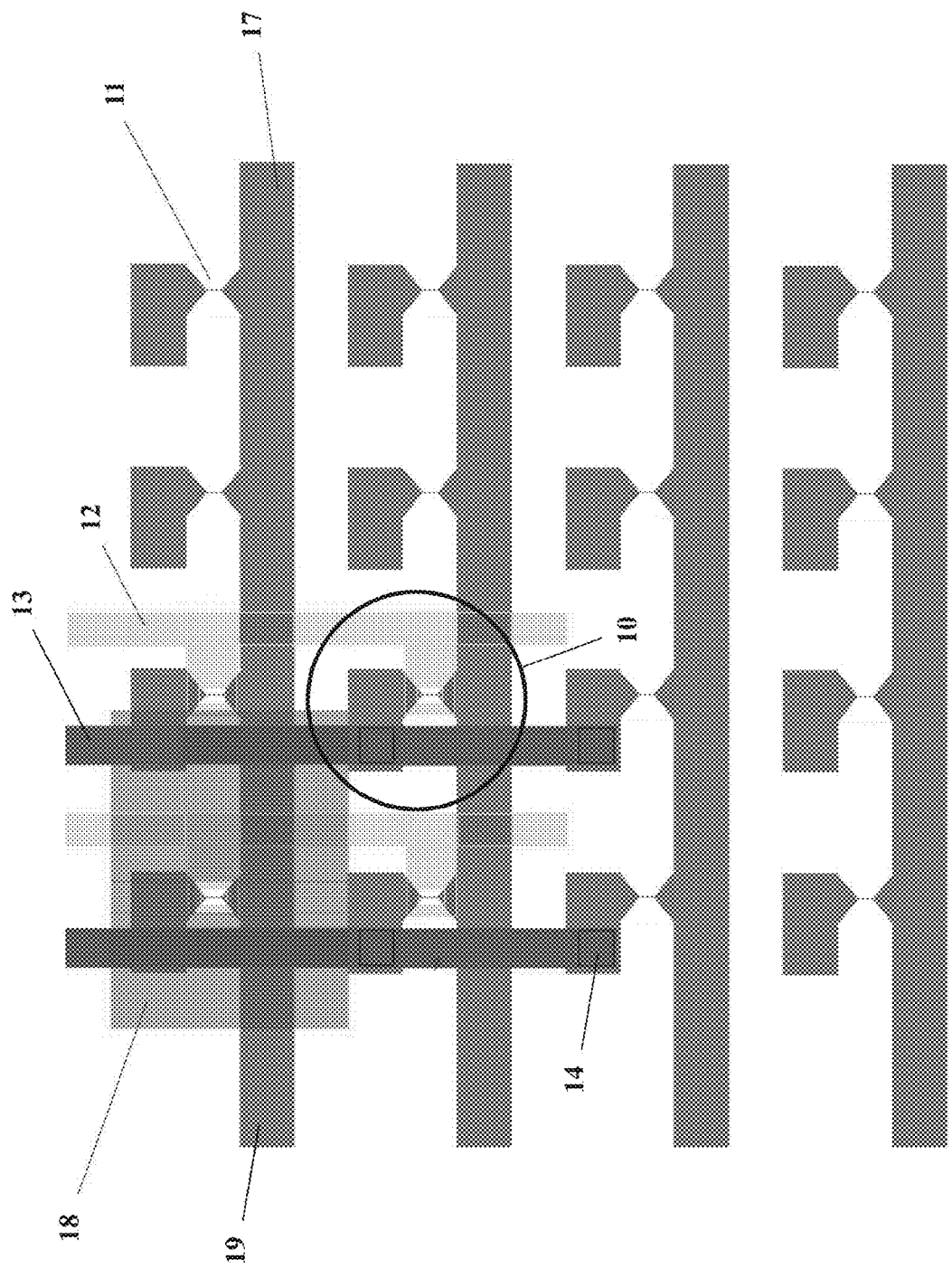
FIG. 7 schematically shows a mask design of the sensor chip including multiple pixels with contact lines of highly-doped silicon and having intrinsically-doped SiNWs, which are decorated with optoelectronically active particles.

FIG. 7 shows a mask design of the sensor chip including multiple pixels (10) contacted by highly-doped silicon contact lines (17) and having an intrinsically doped SiNWs (11), which are decorated with OAPs. One common metal electrode (12), such as gold or platinum, feeds the pixels with the high-frequency AC signal. There is a one common source lead (19) connecting the implanted sources of the pixels to the circuit. The drain contact (14) of each individual pixel is connected to the circuit via the drain leads (13). As mentioned above, each pixel is passivated with a passivation layer (18) leaving only the gate area open for sensing. The reference electrode (not shown here) may be placed outside of the chip or integrated in the chip, as demonstrated above. The excitation light source (not shown here) may also be placed outside the chip, on top of the chip, as shown above.

The pixel array could be fabricated in a CMOS process with pre-processing and post-processing steps using a complete SOI CMOS process, where the top silicon layer is used as an active CMOS layer. In that case, the only post-processing is needed for the counter electrode, the reference electrode and the passivation layer. Alternatively, the pixel array can be fabricated using a standard CMOS process. In that case, the pre-processing is needed to define the silicon nanowire from an SOI wafer covering it by $Si_3N_4$ and then etching the rest of the surface down to the handle wafer. Then the handle wafer can be used in a standard CMOS process leaving the protected area untouched. This CMOS process is then followed by opening of the $Si_3N_4$ protection and contacting of the SiNWs, the post-processing for the counter electrode, the reference electrode and the passivation layer.

The passivation process of the pixel can be carried out by the method of atomic layer deposition (ALD) of the gate oxides, which are deposited directly on the pixel surface leaving only the gate area open for sensing. These gate oxides are excellent sensing interfaces due to high density of their active surface groups obtained in the surface activation process prior to surface functionalisation. The front gate voltage is applied through a reference electrode immersed in electrolyte solution on top of the gate oxide or by a surface-engineered reference electrode on chip. Thus, the thick passivation layer on the contact leads is necessary for a reliable operation of the sensor in different electrolyte solutions as well as to avoid interfering with the signal at the gate oxide.

C. Ahn et al (2014) demonstrated that light can increase sensitivity of the SiNW-based sensors. They showed in the experiments on glucose detection with a SiNW ISFET sensor that electrical current in the SiNWs is increased by photo stimulation. This is simply because incident light actually increases the amount of carriers in the SiNW, although the electron/hole pairs are only generated in the fully depleted nanowire part, not in the contact lead areas. Such photo-stimulation is similar to the light addressable potentiometric sensing (LAPS) phenomenon, when photo-current is generated in the depletion layer of silicon and then detected. Amount of the obtained photocurrent is dependent on the surface potential at the light-excitation point. C. Ahn et al (2014) further showed that the current in the nanowires is increased by photostimulation, which also increases sensitivity of the glucose detection assay in their experiments. For fabrication of their sensors C. Anh et al. (2014) used a transfer process of etched SiNWs onto pre-processed handle wafers. So far, this phenomenon has never been applied to pre-structured substrates, such as with silicon-on-insulator (SOI) wafers.

Thus, there are two different ways to couple the light excitation with electronic effects in a SiNW: either by creating a photoeffect in a SiNW as described above, or by coupling surface plasmons to the nanowire. Regarding the direct photoeffect, it is well known that light can only be absorbed when the energy of the absorbed photon (E=hv) is large enough for an electron to be excited into the valence band. In that case, E is the photon energy, h is Planck's constant and v is the frequency of the photon. The frequency is coupled to the wavelength λ of light by the constant speed of light c=λv. Typically the bandgap of silicon at room temperature is 1.12. eV, which means that silicon becomes transparent for wavelength larger than 1240 nm, which is the near infrared range. For smaller wavelength (i.e. larger energy of the photons), electron hole pairs are generated leading to a photocurrent. In the fully-depleted, intrinsically doped SiNW structures, this results in a higher charge carrier density and consequently, higher sensitivity as described by C. Anh et al. (2014). For these structures, light is adsorbed in the whole visible range making such devices ideal photodetectors. The mechanism that allows the silicon nanowires to become photosensitive to irradiation with light has already been described in literature. In the direct photo effect, it can be tuned by the size, crystalline direction and surface termination. These effects originate from one-dimensional quantum confinement of electrons in these nano sized structures.

Although irradiation of a SiNW with light of larger wavelengths with photon energies below the bandgap does not have enough energy to excite carriers from the valence to the conduction band in bulk silicon, the electron/hole pairs can also be generated between the valence band and surface states, and the donor-like surface trap states can still be formed. The electrons actually deplete the holes trapped at the surface and hence, modulate the gate field. The photogenerated holes are confined to the centre of the SiNW by the gate field, where they increase the conduction of the nanowire, because of the band bending. The holes increase the silicon nanowire conductivity for a certain lifetime until they are trapped (recaptured) at the surface. The gain of the SiNW ISFET can be extremely huge if this re-trapping lifetime is much longer than the holes transit time.

Another approach of coupling excitation light with the aforementioned electronic effects in the SiNWs is a formation of the localised surface plasmons on a surface of OAPs. As a result of irradiating the surface of the OAPs with light having the wavelength comparable or smaller to their size, they become electronically coupled to the nanowire. Thus, the SiNWs of an embodiment are decorated with OAPs to produce a localised surface-plasmon resonance (LSPR) effect and consequently enhance sensitivity of the pixel-based optoelectronic sensor of an embodiment. The sensor therefore combines sensing by means of plasmonics and electronics, utilising two phenomena:

1) OAPs can form a Schottky junction with silicon, and
2) OAPs can create a LSPR on the sensing surfaces of the SiNW.

Reference is now made to FIG. 8 (a) which illustrates the LSPR phenomenon based on the collective oscillation of metal free electrons in the electron cloud in phase while varying an electrical field of incident light. For the case of localised surface plasmons, light interacts with particles much smaller than the incident wavelength. This leads to a plasmon that oscillates locally around the nanoparticle with a frequency known as the LSPR frequency. Metal nanoparticles create LSPRs with very large optical cross sections in the visible and near-infrared (near-IR) spectrum or tailored to absorb in the IR range. The excitation wavelength is dependent on the specific metal material and on its shape. Due to the LSPR created in response to the electromagnetic field of the incident light, the metal nanoparticles drive a collective oscillation of the electrons, which excite the semiconductor electrons and holes by Förster resonance energy transfer (FRET), and/or charge carrier transfer. This enables the creation of active electrons and holes in the semiconductor even in the absence of any direct light absorption described above.

As shown in FIG. 8 (b), metal-silicon Schottky junction results from the contact of the metal with silicon and forces the electrons and holes to move in different directions once they are created inside or near the Schottky junction. This provides a fast lane for charge transfer and suppresses the electron-hole recombination. A space-charge region is created since energy-wise electrons better diffuse into silicon or holes diffuse into the metal to build up an internal field pointing away from the silicon into the metal. When light irradiates the nanoparticle, LSPR-excited electrons in the metal receive a sufficient energy to travel across the space-charge region and to be fed into the conduction band of silicon, thereby increasing the electric signal and in turn assisting in the chemical reaction to take place at the surface of the nanoparticle. Therefore, the LSPR becomes very sensitive to changes in the local dielectric environment. Any reaction at the surface of the metallic nanoparticle would immediately result in a dielectric dipole change and in a change of the induced electric current. This effect scales strongly with diameter of the silicon nanowires becoming more effective when the remaining bulk silicon gets smaller.

The FRET mechanism provides very efficient coupling between optically excited nanoparticles and silicon nanowires. The FRET actually originates from the Coulomb interaction between an OAP and a SiNW and does not require the tunnelling. From the SiNW point of view, exciton energy flows from a significantly large band-gap nanoparticle donor to the SiNW with a smaller band gap acceptor. By definition, an "exciton" is an excited quasiparticle in a solid, which is formed by a Coulomb-bound electron-hole pair.

Metal nanoparticles can be considered as zero-dimensional particles. They have strong and isotropic optical absorption, whereas one-dimensional SiNWs can carry an electrical current and deliver optoelectronic energy to a sensor circuit. Therefore, FRET between metal nanoparticles and SiNWs is an efficient energy-transport mechanism enhancing the rate of exciton generation in the SiNWs due to energy channeling from the metal nanoparticles.

Thus, excitons generated in the metal nanoparticles instantly flow to the SiNW due to the FRET. In such a way, exciton energy becomes harvested in the SiNW. Since the SiNW is connected to a circuit via drain and source electrodes, the exciton energy-harvesting effect can be observed as an enhanced photocurrent or photovoltage. The photocurrent response is observed in a SiNW with an applied external bias and is proportional to the number of electron-hole pairs generated in the SiNW. The photovoltage signal can also appear without an applied external bias if the SiNW contains a built-in electric field p-n junction or Schottky barrier that spatially separates electron-hole pairs (excitons). In the latter case, the signal also depends on the number of optically generated electron-hole pairs.

In a particular embodiment, the OAPs are metal nanoparticles selected from Ag, Cu, Au, Al, Pd, Pt, Ni, Co, Pb, Ti, Fe and Cr, preferably Au or Ag. In a further embodiment, the metal nanoparticles may have the geometry of nanorods or shapes having multiple axes of symmetry. In fact, not only the size, but also the shape of a metal nanoparticle dictates the spectral signature of its plasmon resonance. In fact, the shape of metal nanoparticles affects the local electrical field in a way that a strong enhancement of the local electrical field is present at the location of an abrupt shape change, and the amount of this enhancement is usually larger than that in a nanosphere of the same volume. Since there might be different contact states between the metal and the SiNW, the peak plasmon resonance wavelength varies with embedded states resulting in a better utilisation of the broadband light source.

In addition, because the strong plasmonic near-field from metal nanoparticles is driven parallel to the polarisation and not in the direction of light propagate from a light source, any metal nanoparticle resided on the SiNW surface will provide poor plasmonic contribution to the absorption. On the other hand, SiNWs decorated with metal nanoparticles can efficiently harness surface plasmons by satisfying the geometrical constraint of orthogonality between the plasmonic near-field and the direction of light propagation. With metal nanoparticles spread along the SiNW body (in a parallel orientation), the strong near-field intensity excited from light traveling along the direction of the SiNW is directed into its surface, thereby generating a local density of photocarriers and resulting in efficient plasmonic near-field coupling.

The method used to decorate the SiNWs with metal nanoparticles, for example gold, comprises the steps of preparing the sensor chip, on which SiNWs are clean and free of organic contaminants, and etching native silica in hydrogen fluoride aqueous solution to form the hydrogen terminated silicon surface, which is a chemically passivated silicon substrate whose native oxide thin film is removed by etching, leaving the surface silicon atoms covalently bonded to hydrogen (forming silyl groups on the surface). The silyl groups on the SiNW surface can further react with molecules that have terminal unsaturated bonds or diazo groups in a hydrosilylation reaction. Consequently, organic molecules and biomolecules can be introduced onto the SiNW surface by the hydrosilylation of a hydrogen-terminated SiNW surface.

Thus, the superior sensitivity of a SiNW coated with OAPs is mostly attributed to the effective carrier separation originating from the SiNW full depletion. As a result, a rectifying current is generated between a SiNW and an OAP that are joined by the Schottky junction, when electrons and holes inside the SiNW start moving in opposite directions.

In another particular embodiment, the OAPs are metal oxide nanostructures, such as nanoparticles, nanoclusters, nanorods or nanoflowers made, for example, of CuO, $ZnO_2$, $In_2O_3$, $SnO_2$, IZO, GZO, ITO, IGZO, IZTO or ZTO, preferably $ZnO_2$ nanoclusters. As is the case with the metal nanoparticles, decoration of the SiNWs with metal oxide nanostructures also significantly enhances sensitivity of the pixel-based sensor of an embodiment and constitutes another embodiment. The growth of SiNWs and ZnO nanoclusters of an embodiment is carried out by means of a two-step deposition. As mentioned above, SiNWs are fabricated by the top-down method via a dry reactive etching and wet metal-assisted etching techniques. The ZnO nanoclusters are grown on the SiNWs using atomic layer deposition, pulsed laser deposition or metal-organic chemical vapour deposition.

The mechanism of photocurrent generation in SiNWs decorated with metal oxide nanostructures is very similar to the same mechanism for metal nanoparticles, described above, including forming and breaking of excitons and the charge separation. The charge carriers are photogenerated in both regions of the SiNWs and in the metal oxide nanostructures, when light is irradiating the SiNW. Holes photogenerated in the SiNW cannot pass through the junction potential barrier corresponding to the valence band offset, whereas electrons photogenerated in the metal oxide nanostructure transport toward the opposite site (or toward the positive electrode) in the internal electric field. Simultaneously, the current is rectified, photogenerated electrons in the SiNW and holes in the metal oxide nanostructure transport to positive and negative electrode, respectively. Consequently, the photogenerated charge carriers contribute to the photocurrent of the photodiode.

For operating the optoelectronic pixel, a front gate voltage ($V_{FG}$) is initially applied by a reference electrode, such as Ag/AgCl electrode, which is needed for the front gate contact to keep the electrochemical potential drop over the electrode-electrolyte interface stable (as a result, to keep the electrochemical potential of the solution stable) and the readout signal reliable. The reference electrode is actually set to ground potential in the electronic configuration of an embodiment, and the source and drain potentials are applied at the respective contacts in the circuit. When a sufficient bias potential is applied to the front gate with respect to the back gate, an electric current is immediately induced in the SiNW between the source and drain electrodes. The magnitude of the drain current is determined by an effective electrical conductance of the SiNW and the voltage applied between the source and drain electrodes ($V_{DS}$). The conductance of the SiNW between the source and drain is modulated by the current at the gate (reference electrode). After that, a chopping light frequency (on-off) is applied on top of the chip. When the light frequency matches the AC impedance frequency of the SiNW, the optoelectronic resonance immediately takes place.

The optoelectronic resonance on the SiNW surface is completely a new phenomenon which has recently been discovered by the authors of this application while stepping various light frequency in the range of 0-10 kHz during excitation of the bare SiNWs. This phenomenon has never been disclosed, and it will be demonstrated in the Examples section of the present application. The authors believe that the optoelectronic resonance will greatly contribute to development of optoelectronics and biomedical sensing. Advantages of the optoelectronic resonance are clear and include a significant increase of the current amplitude in the resonance mode. This results in an increase of the detection sensitivity and signal/noise ratio, allows overcoming the Debye length limitations and introduces an additional detection element to the optoelectronic pixel sensing.

Figure 9:
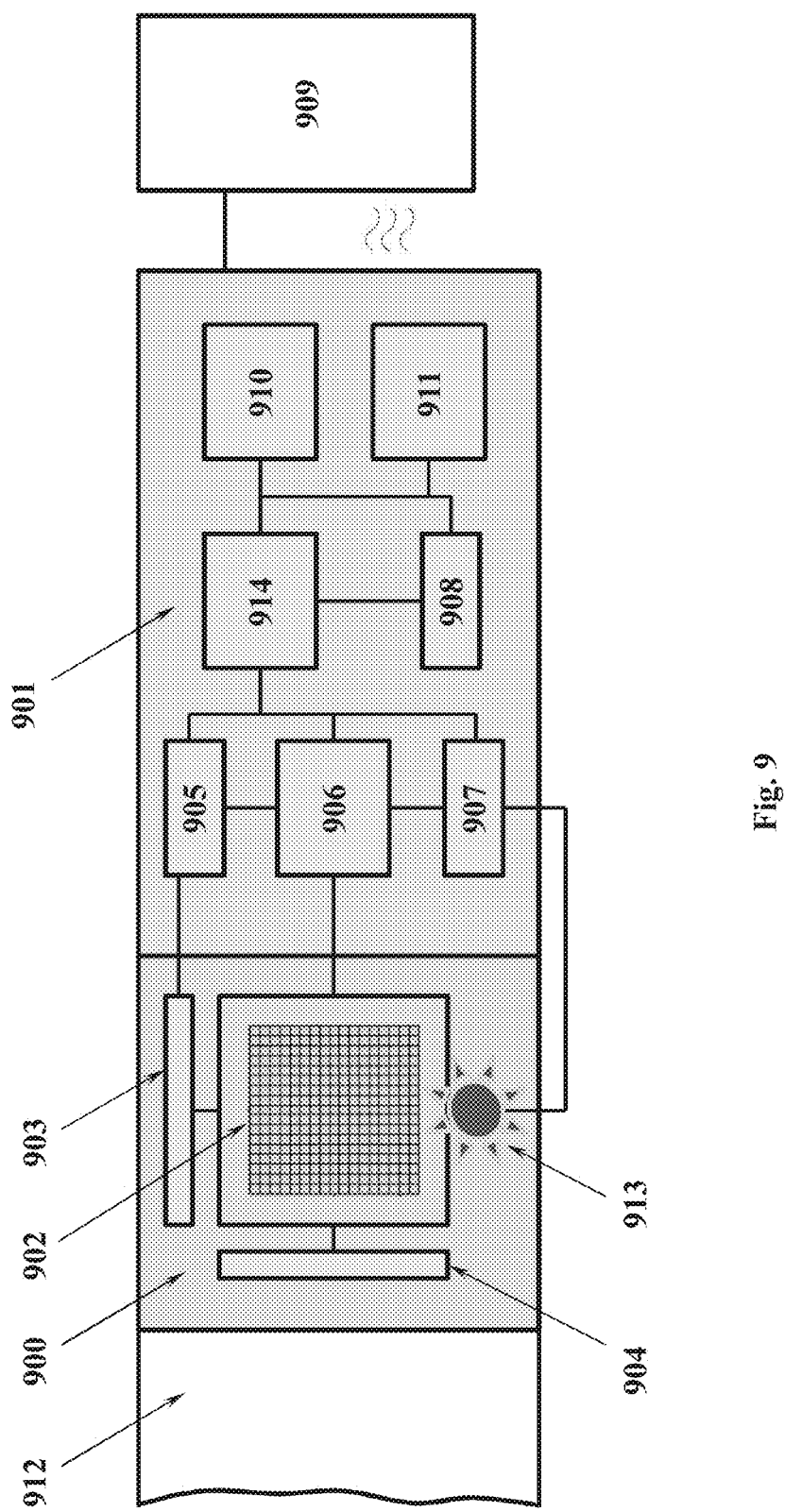
FIG. 9 schematically shows an optoelectronic pixel-based sensor of an embodiment.

In another aspect, FIG. 9 illustrates an optoelectronic sensor comprising a disposable unit (900) mounted on a chip substrate, a reader unit (901) mounted on a flexible printed circuit board (PCB), and an excitation light source (913), wherein 1) the disposable unit (900) comprises:
   a pixel array (902) of an embodiment comprising a plurality of pixels arranged in rows and columns and exposed to medium for sensing;
   a row decoder (903) connected to said pixel array (902) for addressing a plurality of said pixels arranged in rows; and
   a column decoder (904) connected to said pixel array (902) for addressing a plurality of said pixels arranged in columns; and
2) the reader unit (901) comprises:
   a voltage source (905) connected to an electric circuit for supplying electric power to the sensor;
   an integrated or CMOS current amplifier (906) connected to said pixel array (902) for amplification of an electric current obtained from the pixels;
   an integrated function generator (907) for modulating said light source (913);
   a microcontroller (914) with in-built digital input/output for processing, converting the received signal into data readable in a user interface (909), and outputting the converted signal to said user interface (909); and
   a connection module (910) for wired connection of the sensor to said user interface (909); or a wireless connection module (911) for wireless connection of the sensor to said user interface (909).

In a particular embodiment, the sensor further comprises a battery (908) for powering the microcontroller (914). In a specific embodiment the wired connection module (910) is USB. In another specific embodiment, the wireless connection module (911) is NFC, Bluetooth®, Wi-Fi or GSM. The Bluetooth® or NFC technology provides the wireless communication between the sensor and the user interface (909) for up to 20 meters. In case of Wi-Fi, the connection between them can be established for up to 200 m, while the GSM module allows the worldwide communication.

In another particular embodiment, the sensor further comprises a microfluidic chip or lateral flow strip (912) for supplying an analyte solution to the pixels array. In general, a microfluidic chip is a set of micro-channels etched or moulded into a material, such as glass, silicon or polymer. A non-limiting example of such polymer, which is used in many different microfluidic chips, includes polydimethylsiloxane (PDMS). The micro-channels forming the microfluidic chip are connected together in order to achieve the desired features, such as mixing, pumping, sorting and controlling the tested environment.

In a further embodiment, the voltage source (905) is a battery, such as AA-battery. Alternatively, the sensor can be powered, for example, either from the USB module (910) or wirelessly via an RFID (Radio-Frequency Identification) tag.

Figure 10:
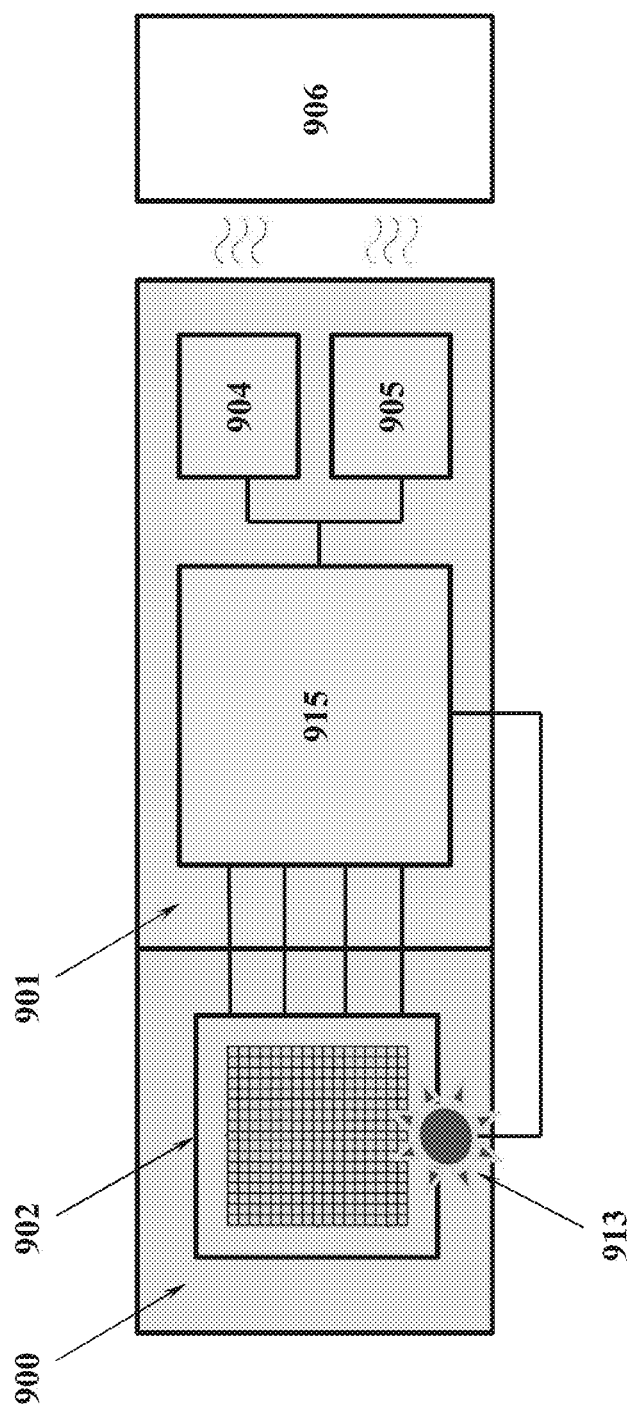
FIG. 10 schematically shows a wearable-patch optoelectronic pixel-based sensor of an embodiment.

In a further aspect, FIG. 10 illustrates a wearable patch sensor comprising a disposable unit (900) mounted on a chip substrate, a reader unit (901) mounted on a flexible printed circuit board (PCB) and an excitation light source (913), wherein
   i. the disposable unit (900) comprises a pixel array (902) of an embodiment comprising a plurality of pixels exposed to medium for sensing; and
   ii. the reader unit (901) comprises:
      an ASIC (Application-Specific Integrated Circuit) chip (915) customised for a particular use of the sensor;
      a battery or power receiver (904) connected to an electric circuit for supplying electric current to the sensor; and
      a wireless connection module (905) for wireless connection of the sensor to a user interface (906).

The ASIC chip (903) may include an amplifier for amplification of an electric current obtained from the pixels, an additional voltage source, such as a battery, for powering the sensor, a function generator for modulating the light source, and decoders.

In another aspect, the optoelectronically active particles decorating the surface of the SiNWs are functionalised with different molecules (herein, "receptors"), which are capable of binding to a target (analyte) molecule, for sensing. Non-limiting examples of the receptors are antigens or antibodies for immunoassays, aptamers, DNA strands, protein receptors or redox enzymes. As a result, the sensor of an embodiment can be used for label-free detection of target (analyte) molecules by monitoring changes in the electric current of the transistor caused by variations in the charge density or the impedance at the gate oxide-electrolyte interface.

In general, charges formed in the liquid medium sensed by the SiNWs are originated from the dissolved molecules. In most cases, the molecular receptors bound to the transistor surface (the SiNW gate oxide in the present case) are separated from this surface by molecular cross-linkers or proteins of approximately 5-15 nm length. Therefore, the aforementioned charges are screened from the sensing surface by dissolved counter ions. As a result of the screening, the electrostatic potential that arises from charges on the analyte molecule exponentially decreases to zero with increasing the distance from the sensing surface. This screening distance is defined as a "Debye length", and it must be carefully selected when designing the ISFET's receptor layer in order to ensure the optimal sensing.

The Debye length limitation can be overcome by modification of the receptors and controlling the immobilisation density over the ISFET's sensing surface. Elnathan et al 2012 described this approach in detail and demonstrated the increased sensitivity of their sensor to troponin detection directly from serum for the diagnosis of acute myocardial infarction. The pixel-based optoelectronic sensor of an embodiment, which operates at high frequencies and utilizes the surface plasmonic resonance effect, can also be used to sense beyond the Debye screening length.

The pixel-based sensor of an embodiment is characterised with respect to its electronic properties and to the measurement configuration for molecular sensing applications. As noted above, similar to the SiNW ISFETs, the main features of the pixel-based sensor are determined by the transfer characteristics and the output characteristics at room temperature.

The transfer characteristics shows the drain current ($I_{DS}$) of the SiNW as a function of the gate-source voltage at constant drain-source voltages. The output characteristics show $I_{DS}$ as a function of the drain-source voltage at constant gate voltages. The transfer characteristic was carried out by sweeping the gate voltage ($V_{FG}$ and/or $V_{BG}$) forward and backward in the range of applied voltage, while the $V_{DS}$ were kept constant. The output characteristic was measured by sweeping the $V_{DS}$ at a constant gate voltage ($V_{FG}$ and/or $V_{BG}$).

In a further aspect, the combined transducer principle defined herein as a "multiparameter readout" includes: DC electronic readout of the sensor, AC electronic readout of the sensor, temperature sensing and photocurrent sensing. The photocurrent sensing involves the use of the light excitation source, such as a photo diode or a laser diode, to generate a photocurrent in the depleted SiNW structure. This can be in distinct colour (for example, using the laser diode for small wavelength bandwidth). The photocurrent can increase a number of charge carriers and hence, the sensitivity of the SiNW. The generated photocurrent can be sensed in the DC voltage readout mode or the light can be modulated and recorded in the AC mode at a distinct frequency.

When the AC stimulation is used, then the combination of methods, for example the combination of the electronic AC mode and optically induced AC photocurrent, can be brought into resonance. This mechanism is distinctly different from the 'normal' photoeffect, as shown in the Examples below. The resonance can be achieved with different colours, for example, blue with 365 nm wavelength, green with 470 nm wavelength or red with 655 nm wavelength. Even near-IR can be used for sensing in whole blood samples with consequent reading in the DC mode and in the AC mode.

EXAMPLES

Example 1: Electroless Growing of Homogenous Gold Nanoparticles on Silicon

The electroless process of growing gold nanoparticles on silicon involves immersion of H-terminated silicon substrate into a metal-salt solution containing HF acid. The nucleation and growth steps involve the galvanic process in which metal ions are reduced to pure metal and the available silicon on the surface is subsequently oxidized to $SiO_2$ and gradually dissolves into the solution. HF is used to dissolve a newly formed $SiO_2$ in order to keep on going the electroless reaction. Further growth of the gold nanocrystal is supported by autocatalysis.

Prior to dipping a substrate into a reaction solution, it is immersed in HF solution to remove a native oxide layer, which may be of 1-3 nm thickness. Therefore, the gold nanoparticles deposition proceeds only on SiNWs but not on the supporting silicon substrate with a thermal oxide layer of about 600 nm thickness. The following redox reactions take place on the silicon surface during the electroless process for the gold nanoparticles deposition:

$$AuCl_4^- + 3e^- \rightarrow Au^0 + 4Cl^- (E^0 = +0.93 \text{ V}) \quad (1)$$

$$Si_{(s)} + 2H_2O \rightarrow SiO_2 + 4H^+ + 4e^- (E^0 = -0.91 \text{ V}) \quad (2)$$

$$SiO_{2(s)} + 6HF \rightarrow H_2SiF_6 + 2H_2O \quad (3)$$

Materials:
Silicon wafer, 1% HF, $HAuCl_4$ (G4022-1G-D), 30% $H_2O_2$, 98% $H_2SO_4$, acetone, isopropanol and deionised water (all chemicals are purchased from Sigma).

Cleaning:
Silicon samples are initially immersed in a beaker filled with acetone to clean them inside ultrasonic bath for 10 minutes. The silicon samples are then transferred to a beaker filled with isopropanol and cleaned inside the ultrasonic bath for another 10 minutes. Further, these samples are transferred to a beaker filled with deionised water and cleaned inside the ultrasonic bath for 5 minutes, followed by drying with a nitrogen stream. Finally, the dried silicon samples are cleaned with piranha solution (2:1 v/v 98% $H_2SO_4$ and 30% $H_2O_2$) for 10 minutes. The piranha solution is carefully pipetted on top of the sample's surface to fully cover it with the liquid.

HF Etching:
The silicon samples cleaned in the previous step are transferred to the cleanroom for 1% HF etching of the silicon dioxide on top of the silicon sample. The samples are dipped into the 1% HF bath. Depend on the thickness of the $SiO_2$ layer on top of the silicon sample, the etching time is varied in order to completely remove $SiO_2$. The experimental etching rate of the thermal $SiO_2$ layer on 1% HF is about 4-5 nm/minute.

Time of etching is calculated based on this rate and measured accordingly. After etching, the samples are cleaned with deionised water, for about 5-7 minutes. The total cleaning time inside deionised water should not excess 15 minutes, otherwise the $SiO_2$ will start growing again. The etched silicon samples are quickly dried in a nitrogen stream.

Figure 11:
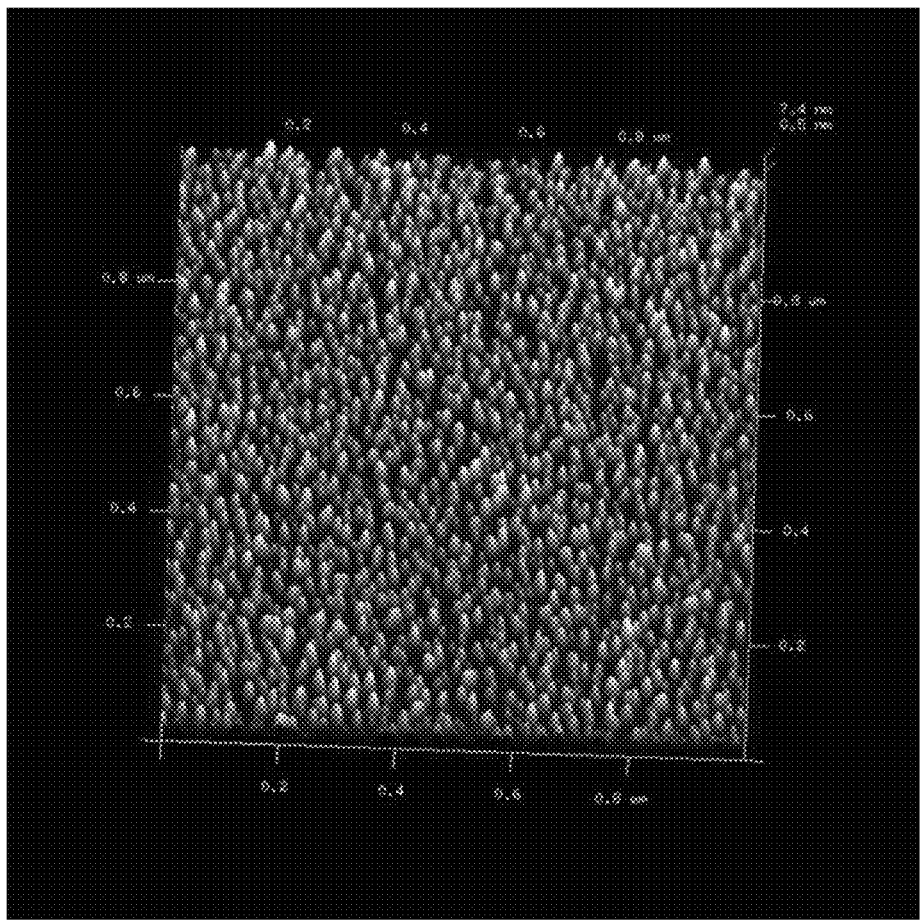
FIG. 11 shows the AFM image of gold nanoparticles having a diameter of 5-7 nm grown homogeneously on a silicon sample.

Growing of Gold Nanoparticles on a Silicon Surface:
0.25 mM $HAuCl_4$ diluted with deionised water is dropped on the sample's surface for exactly 15 seconds. The silicon samples are dipped again into deionised water for final cleaning for 5-7 minutes and then dried with a nitrogen stream. FIG. 11 shows the AFM image of gold nanoparticles having a diameter of 5-7 nm grown homogeneously on a SiNW.

Noteworthy, this method allows a selective deposition of gold nanoparticles on silicon nanowires but not on the $SiO_2$ passivated area.

Example 2: Electrical Characterisation of SiNWs Decorated with Gold Nanoparticles The purpose of this experiment is to investigate the nature of the contact between gold nanoparticles and two types of silicon: n-Si and p-Si. Both types of silicon were decorated with gold nanoparticles as detailed in the above example, followed by an overnight oxygen plasma treatment and then silver glue application. FIG. 12 (a) schematically shows the test system for n-type Si, while FIG. 12 (b) shows the results of electrical scanning of this system. FIG. 13 (a) schematically shows the test system for p-type Si, while FIG. 13 (b) shows the results of electrical scanning of this system.

The electrical measurements shown in FIG. 12 (b) and FIG. 13 (b) demonstrate a quasi-symmetrical current in both wings of both systems with very low hysteresis. This clearly indicates a low Schottky contact between gold nanoparticles and n-Si (R~0.002 Ohm×cm²) and between gold nanoparticles and p-Si (R~1-10 Ohm×cm²).

Figure 14:
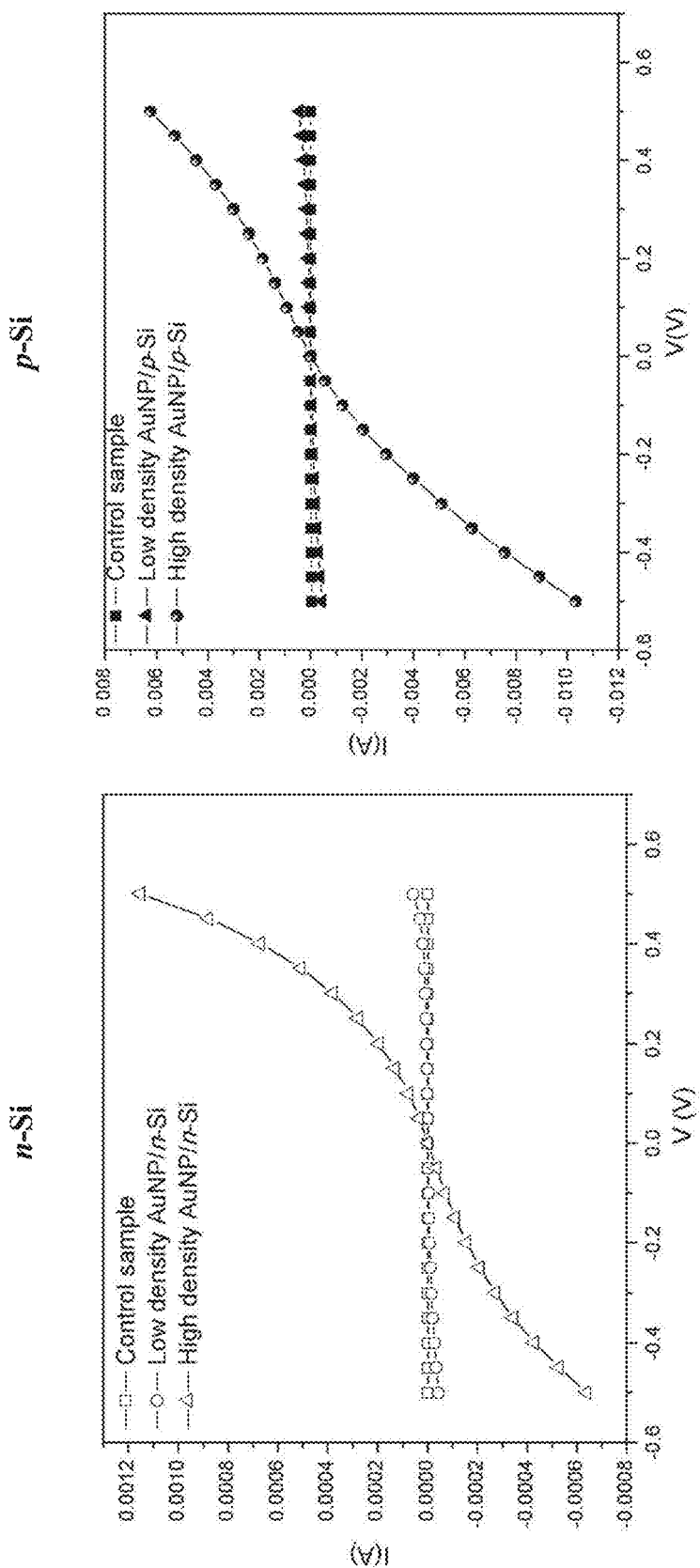
FIG. 14 summarises the results of the experiment presented in FIGS. 12(b) and 13(b).

As can be seen in FIGS. 12 (b) and 13 (b), density (or number) of gold nanoparticles grown on silicon depend on the reaction time: longer reaction time increases the number of gold nanoparticles on the silicon surface. FIG. 14 summarises the results of this experiment presented in FIGS. 12 (b) and 13 (b). A direct electron transfer between gold nanoparticles and silicon does not exist if the contact energy barrier between the gold nanoparticle and silicon is too high. This experiment testing the contact barrier demonstrates that the direct electron transfer can exist. The measurements were performed in both n-Si and p-Si in order to confirm the low contact energy barrier. Thus, electrical measurements of the junction between gold nanoparticles and n/p-type silicon show a very low Schottky contact barrier that clearly indicates the existence of the direct electron transfer.

Example 3: Tunnelling Current in SiNWs Decorated with Gold Nanoparticles

Figure 15B:
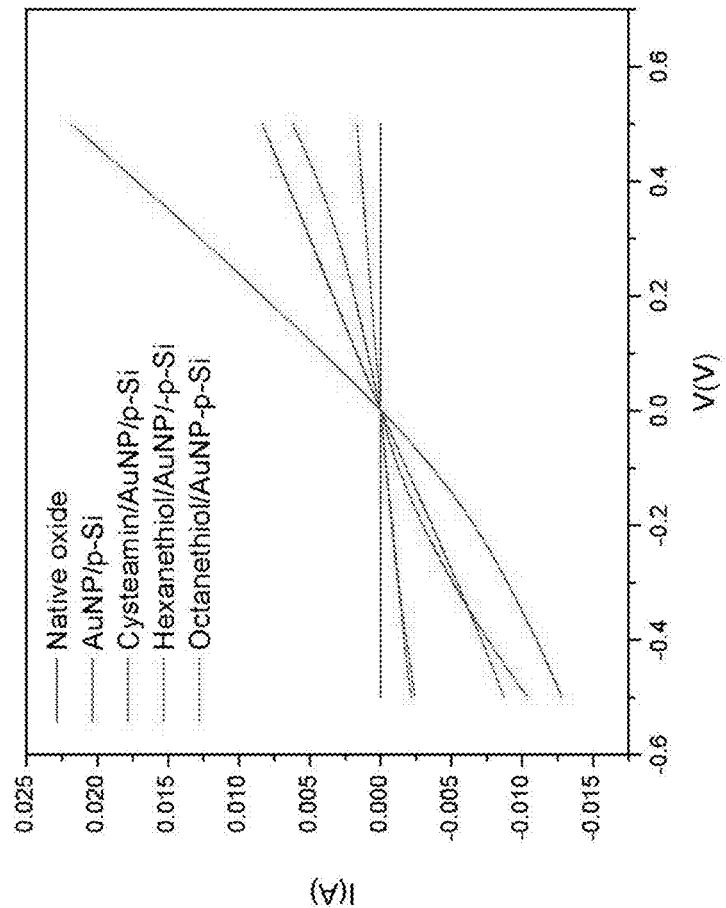
FIG. 15(a) schematically shows the test system for p-type silicon decorated with gold nanoparticles coated with self-assembled monolayers of cysteamine, hexanethiol and octanethiol.
FIG. 15 (b) shows the results of electrical scanning of the system shown in FIG. 15(a).
Figure 15A:
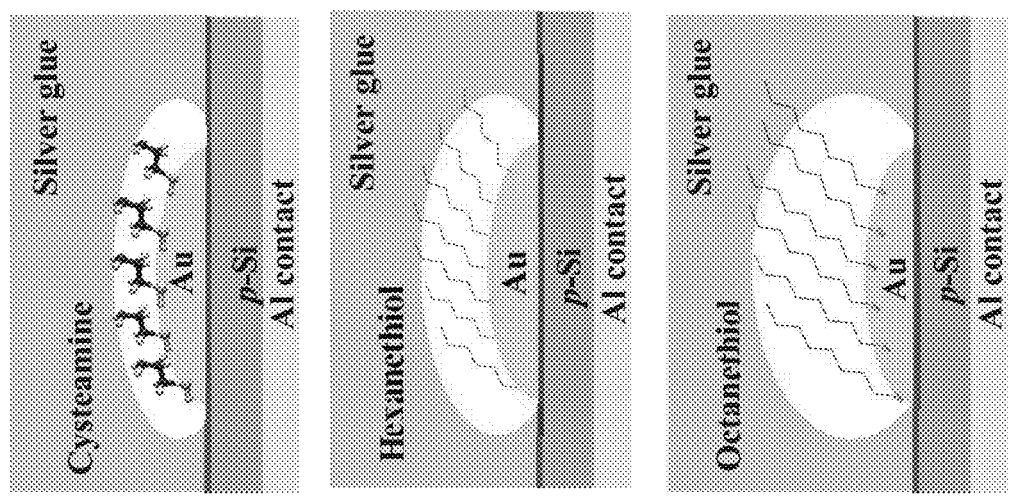
Figure 16A:
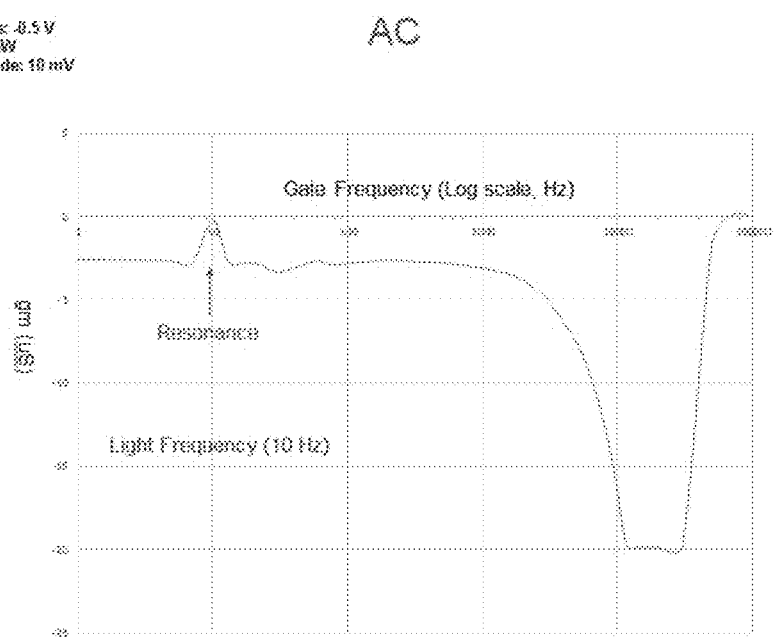
FIG. 16(a)-(d) show the electronic scan of the SiNWs in a transfer function test for light frequencies of 10 Hz, 100 Hz, 1000 Hz and 5000 Hz, respectively (the plots are mirrored at x-axis).
Figure 16B:
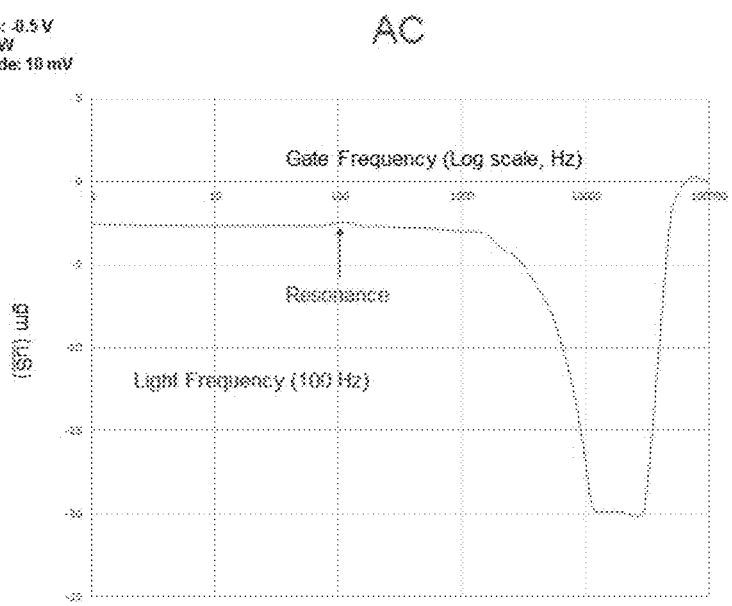
Figure 16C:
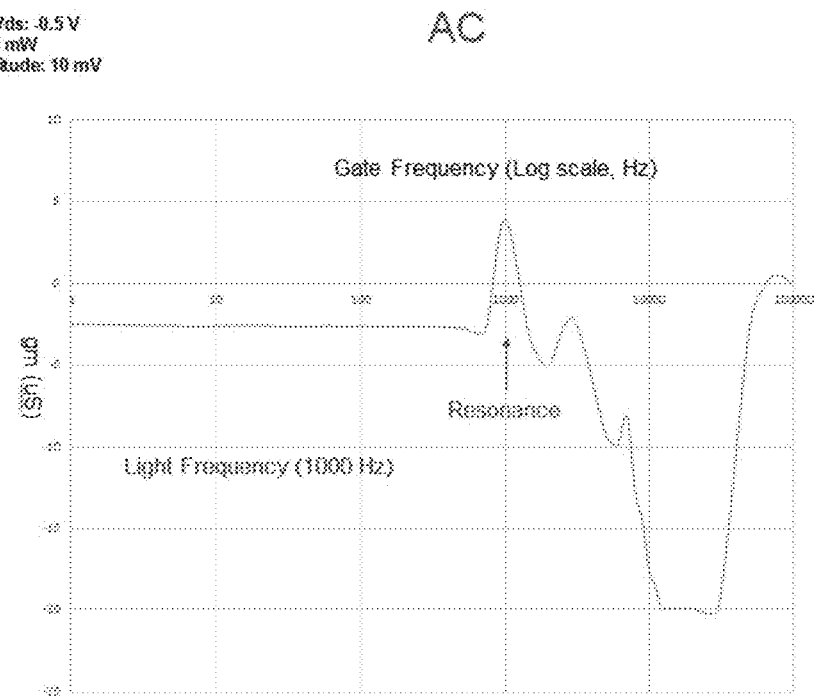
Figure 16D:
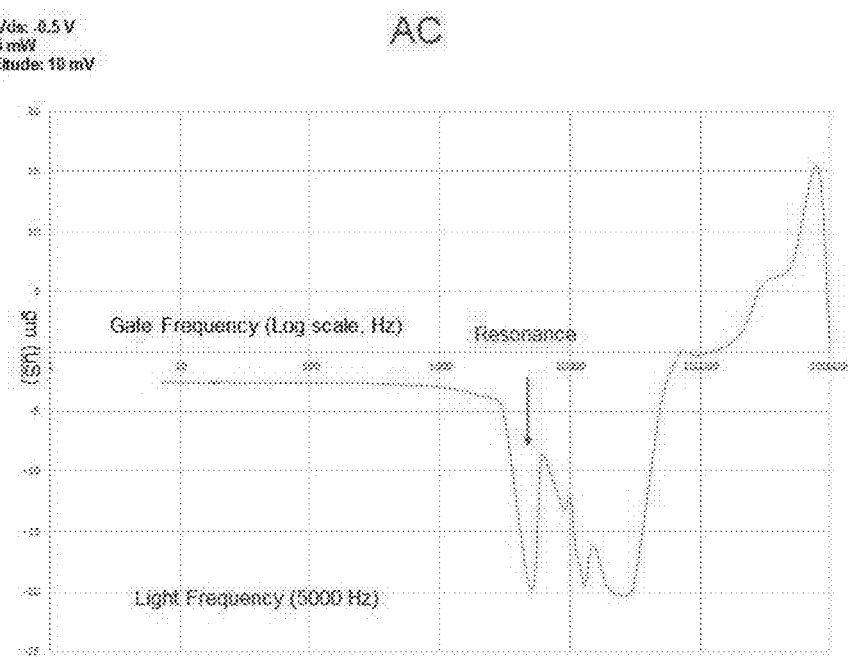

The tunnelling current in a SiNW, resulted from a direct electron transfer, was measured using gold nanoparticles coated with self-assembled monolayers of straight-chain alkyl and alkylamino thiols, such as cysteamine (two carbon atoms in the aliphatic chain), hexanethiol (six carbon atoms)

and octanethiol (eight carbon atoms), as shown in FIG. 15 (a). The results of the electric measurements are shown in FIG. 15 (b).

Silver glue is conductive material and so are the gold nanoparticles. Self-assembled monolayers of cysteamine, hexanethiol and octanethiol act as electrical bridges that electrically connect the silver glue to gold nanoparticles. The obtained results show that longer the alkyl chain, less electrical current flows through the gold nanoparticles and more insulated is the silicon wire. In other words, the measured electric current decreases with increasing the length of the alkyl chain from 2 to 8 carbon items in the self-assembled monolayer. This result is a clear experimental evidence for the direct electron transfer from gold nanoparticles to silicon via functional molecules. In addition, a nearly perfect Ohmic contact can be seen in case of alkyl chains with 6 or 8 carbon atoms. This phenomenon opens a huge potential for forming molecular switches in direct electron transfer between gold nanoparticles and silicon.

Example 4: Optoelectronic Resonance in Bare SiNWs

Discovery of the optoelectronic resonance phenomenon was initially done with the experimental setup described in the present application. A modulated light source (red-light laser diode) was placed on top of the sensor. The SiNWs were then scanned electronically in a transfer function test. During the first trials the two frequency sources (optical and electrical) were not coupled or matched. The results of this experiment are shown in FIG. 16 (a)-(d) for light frequencies of 10 Hz, 100 Hz, 1000 Hz and 5000 Hz, respectively (the plots are mirrored at x-axis). The obtained signal looks like the typical behaviour of coupled oscillator systems. Such systems can be driven to resonance by matching the phase to 90°. However, this was not demonstrated yet in the present preliminary experiment, since two yet independent sources were used in these measurements. Although the phase is shifting by chance in FIG. 16 (a)-(d), the resonance effects are clearly visible. It should be stressed that this is absolutely a new phenomenon that has been recently discovered by the authors of the present application and mentioned herein for the first time.

The next experiment was conducted with the system shown in FIG. 5 (b). This system can be defined as an accumulation mode field-effect transistor with light excitation in a transimpedance amplifier circuit, wherein the transimpedance amplifier includes an operational amplifier (OP) and a resistor. The light excitation circuit of the above transistor includes a light source, a function generator modulating the light source, and a 2-channel lock-in amplifier. Light frequency is modulated with the function generator to match the AC impedance frequency of the silicon nanowire, thereby creating the optoelectronic resonance in the system.

Figure 17A:
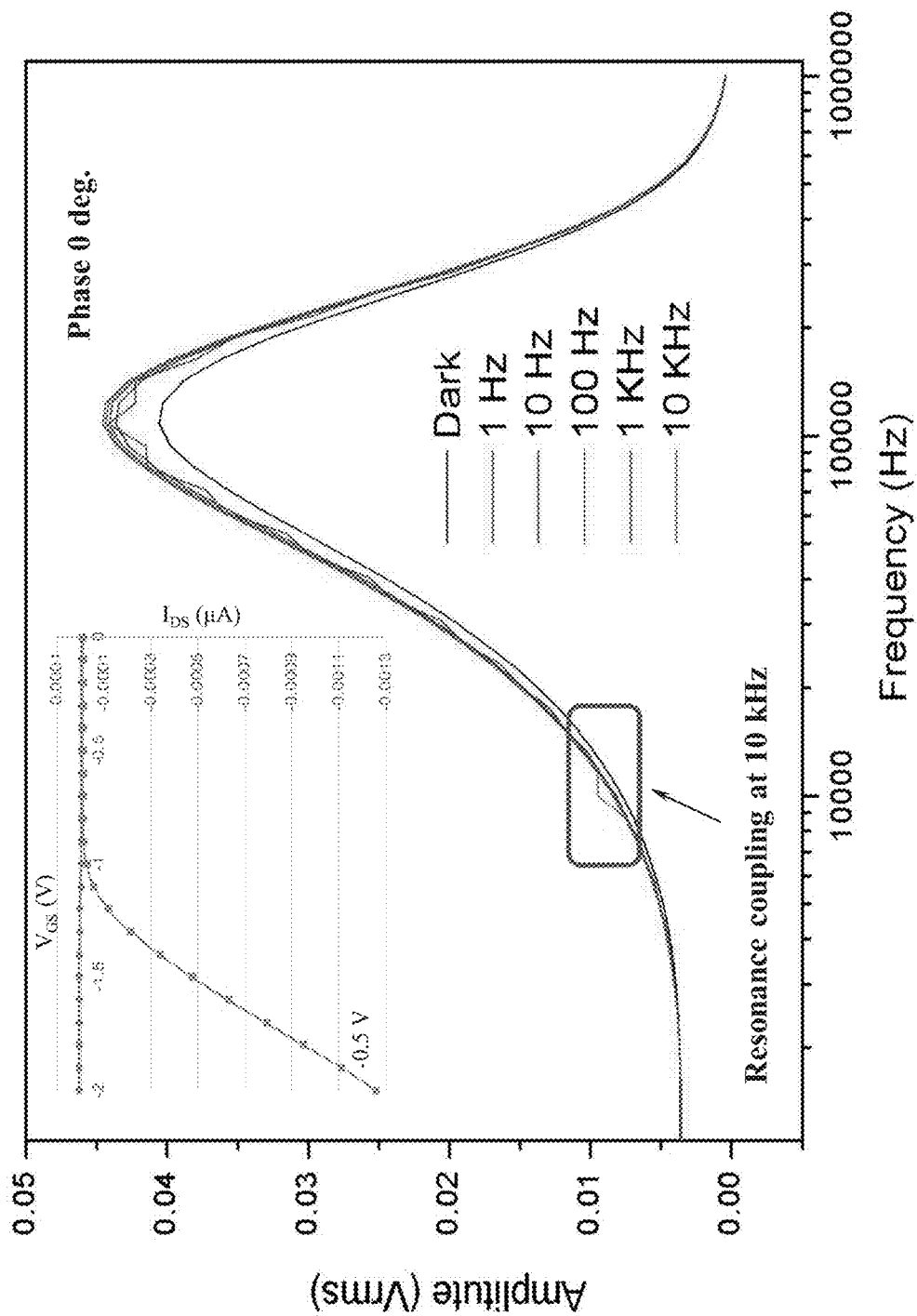
FIG. 17(a) demonstrates the optoelectronic resonance in the SiNW while stepping various light frequency in the range of 0-10 kHz during excitation of the bare SiNWs with UV light of 365 nm wavelength.
Figure 17B:
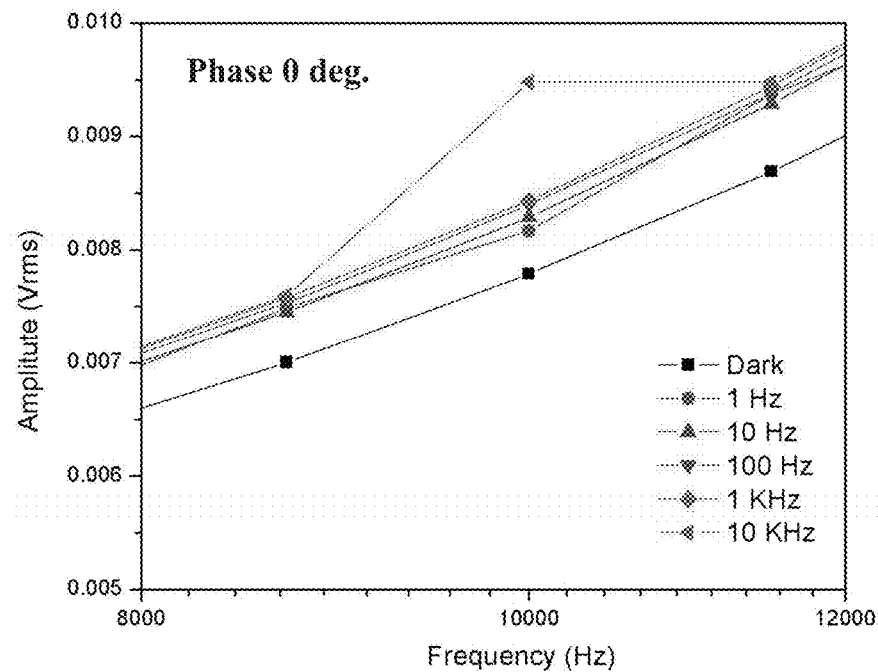
FIGS. 17(b)-(c) show the zoomed-in area of the resonance peak from FIG. 17(a) for 0 deg. and 90 deg. phases, respectively.
Figure 17C:
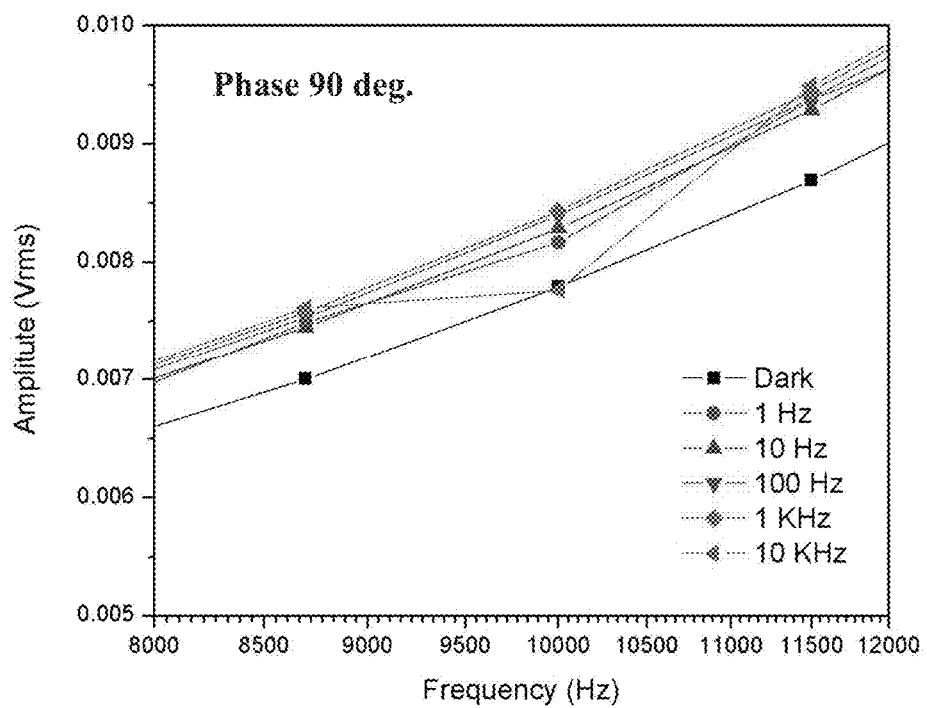

As shown in FIG. 17 (a), the optoelectronic resonance on the SiNW surface was clearly observed while stepping various light frequency in the range of 0-10 kHz during excitation of the bare SiNWs with UV light of 365 nm wavelength. FIGS. 17 (b) and (c) show the zoomed-in area of the resonance peak for 0 deg. and 90 deg. phases, respectively.

Figure 18A:
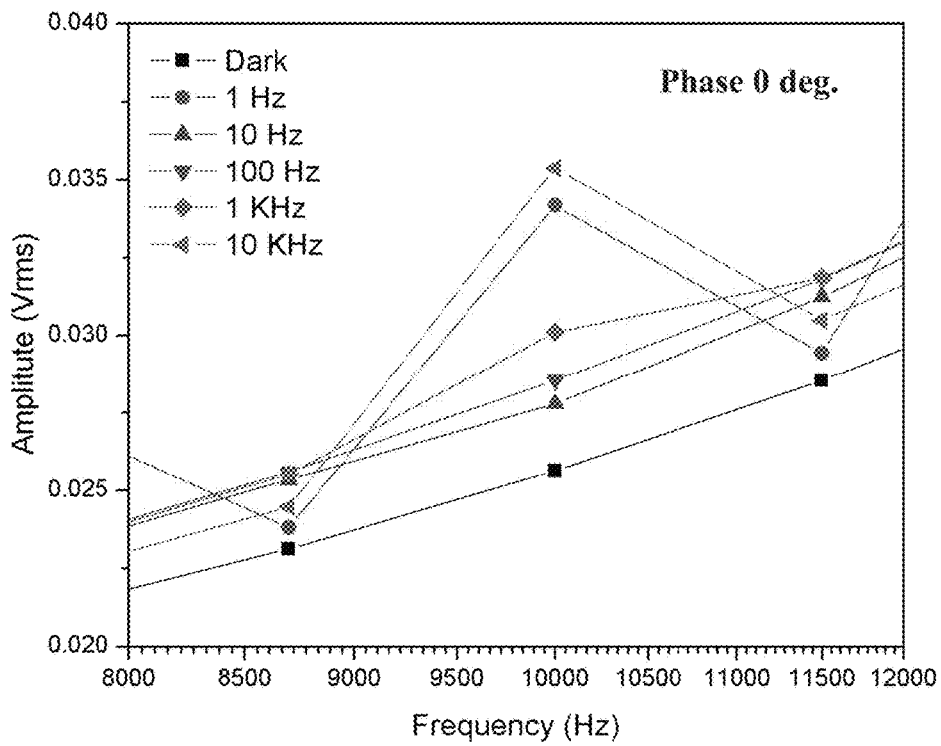
FIGS. 18(a)-(b) show the zoomed-in area of the resonance peak for 0 deg. and 90 deg. phases, respectively, for excitation of the bare SiNWs with red light of 655 nm wavelength.
Figure 18B:
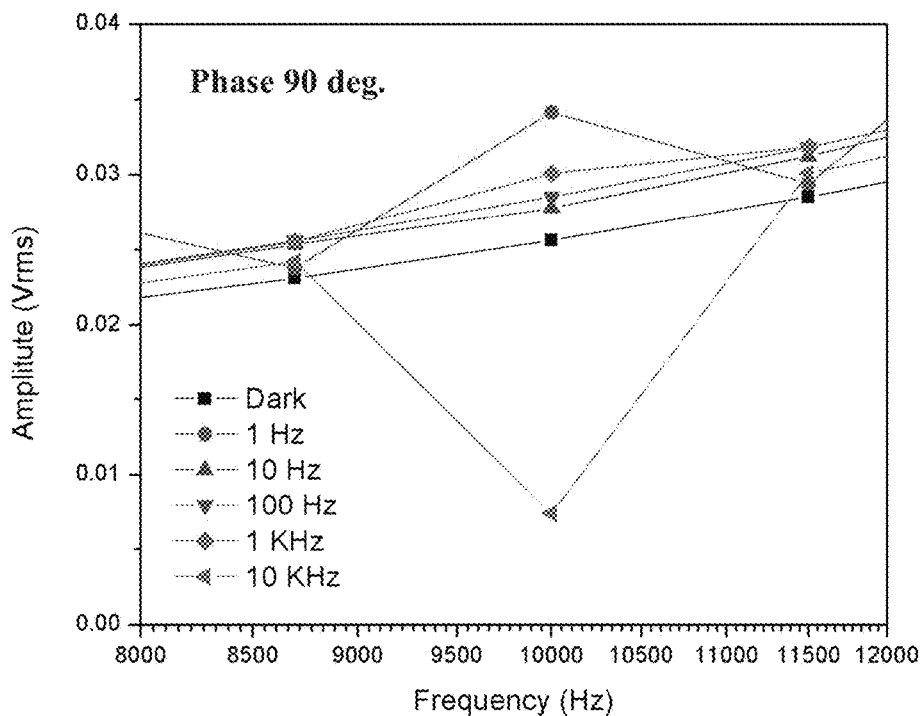
Figure 19A:
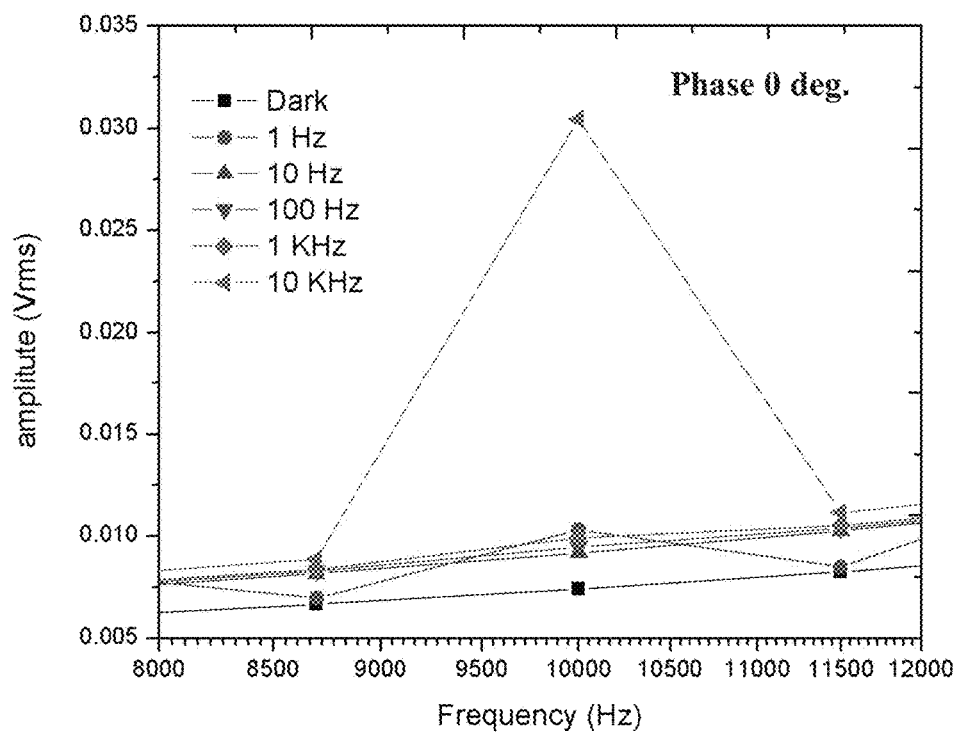
FIG. 19(a) shows the zoomed-in area of the resonance peak for 0 deg. phase, for excitation of the bare SiNWs with green light of 470 nm wavelength.
Figure 19B:
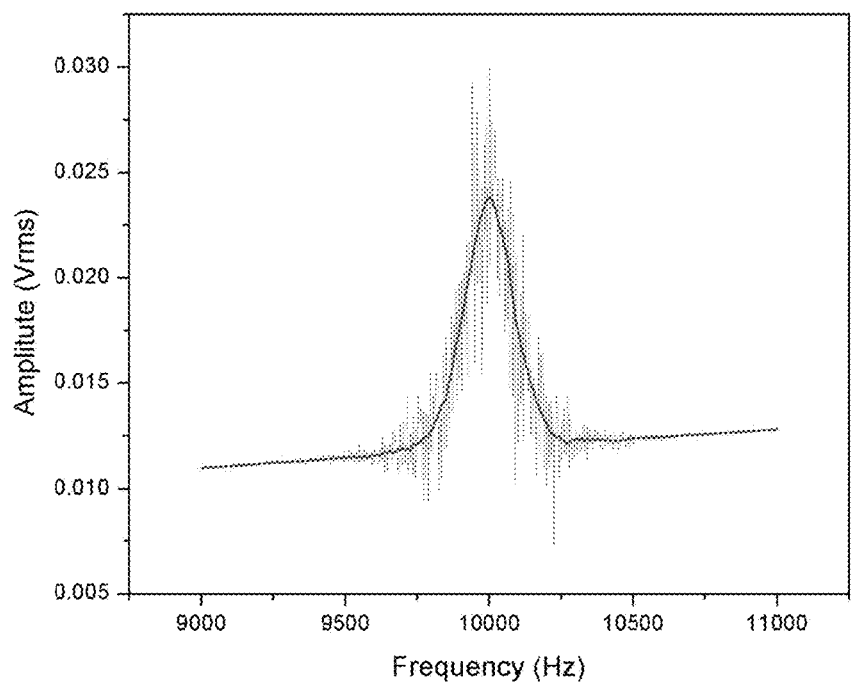
FIG. 19(b) shows the optoelectronic resonance at 10 kHz of FIG. 19(a) for 1000 data points.
Figure 20:
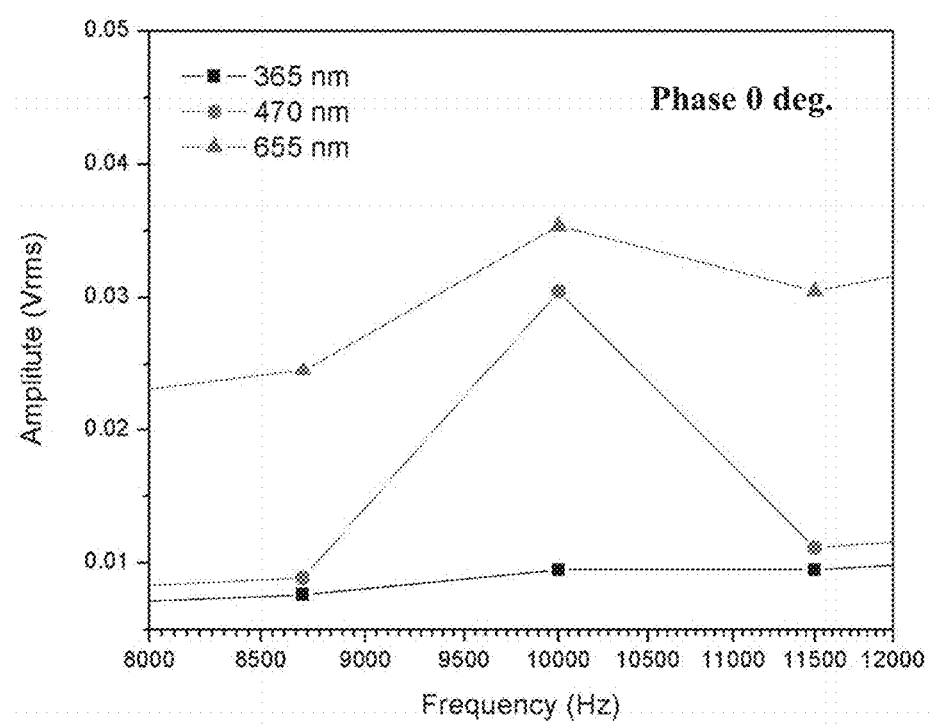
FIG. 20 shows the resonance coupling peak at 10 kHz (phase 0 deg.) at different excitation light wavelengths (summary of FIGS. 17(b), 18(b) and 19(b)).

FIGS. 18 (a) and (b) show the zoomed-in area of the resonance peak for 0 deg. and 90 deg. phases, respectively, for excitation of the bare SiNWs with red light of 655 nm wavelength. FIG. 19 (a) shows the zoomed-in area of the resonance peak for 0 deg. phase, when the bare SiNWs is excited with green light of 470 nm wavelength, while FIG. 19 (b) shows the same optical AC impedance (optoelectronic) resonance at 10 kHz for 1000 data points. FIG. 20 plots the resonance coupling peak at 10 kHz (phase 0 deg.) at different excitation light wavelengths.

Example 5: Optoelectronic Resonance in SiNWs Decorated with Gold Nanoparticles

Figure 21A:
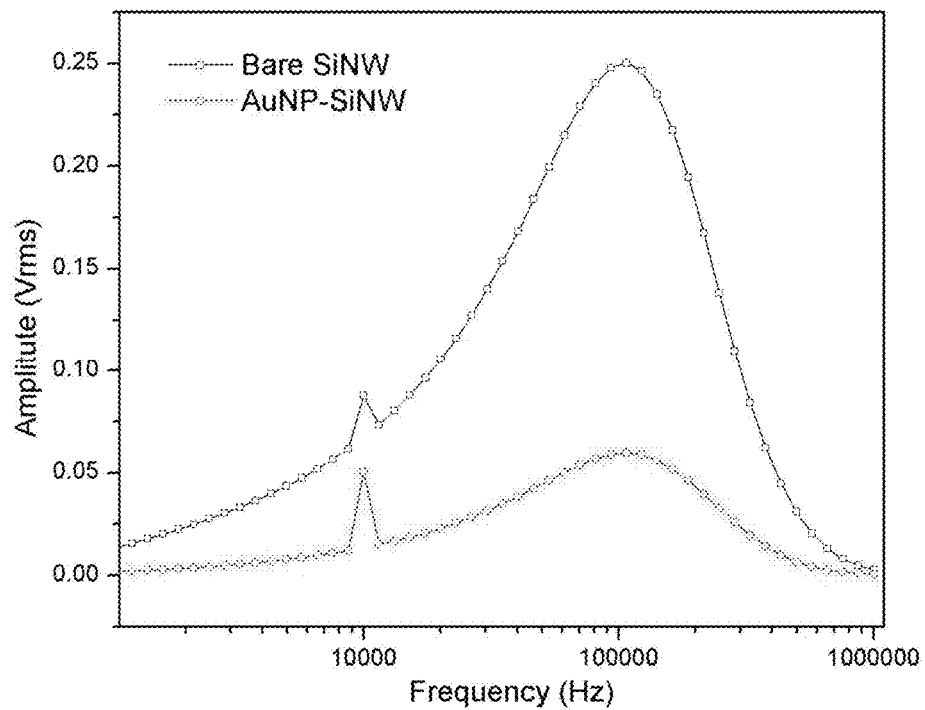
FIG. 21(a) shows the optoelectronic resonance peak in bare silicon and in the silicon decorated with gold nanoparticles after irradiation at 470 nm.
Figure 21B:
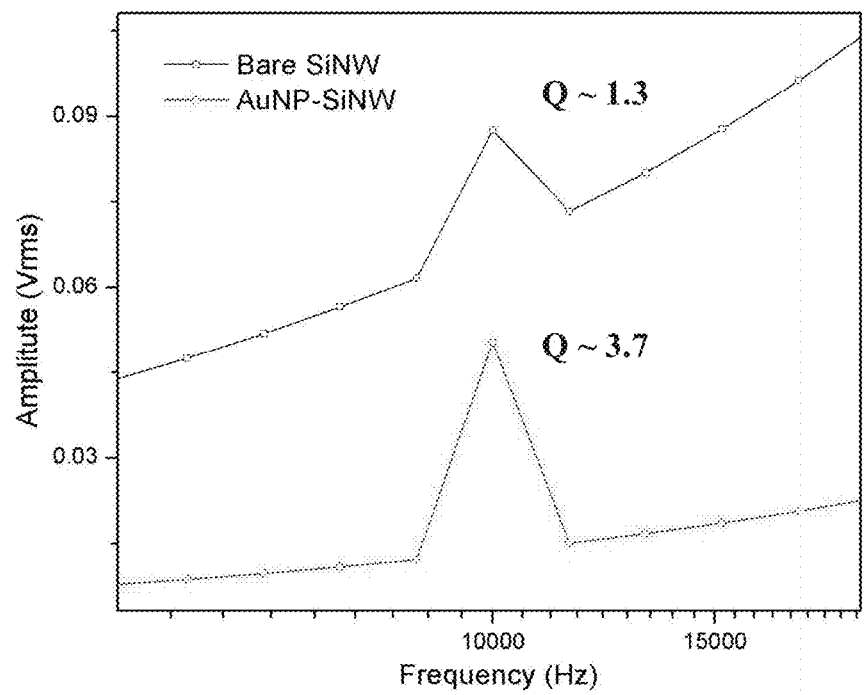
FIG. 21(b) shows the zoomed-in area of the resonance peak of FIG. 21(a).

Even stronger optoelectronic resonance has been observed in SiNWs decorated with gold nanoparticles. FIG. 21 (a) shows the optoelectronic resonance peak in bare SiNWs and in the SiNWs decorated with gold nanoparticles after irradiation at 470 nm, and FIG. 21 (b) shows the zoomed-in area of the peak. Q-factor (quality factor), which characterises a resonator's bandwidth relative to its centre frequency (how under-damped an oscillator or resonator is) and corresponds to a signal/noise ratio, of bare SiNWs is calculated at 10 kHz and found to be approximately 1.3, while the Q-factor for the decorated SiNWs is about 3.7. Such significant increase of about 280% can be attributed only to the plasmonic effect appearing on the surface of the gold nanoparticles.

Example 6: Finding a Wavelength of Optoelectronic Resonance

Figure 22A:
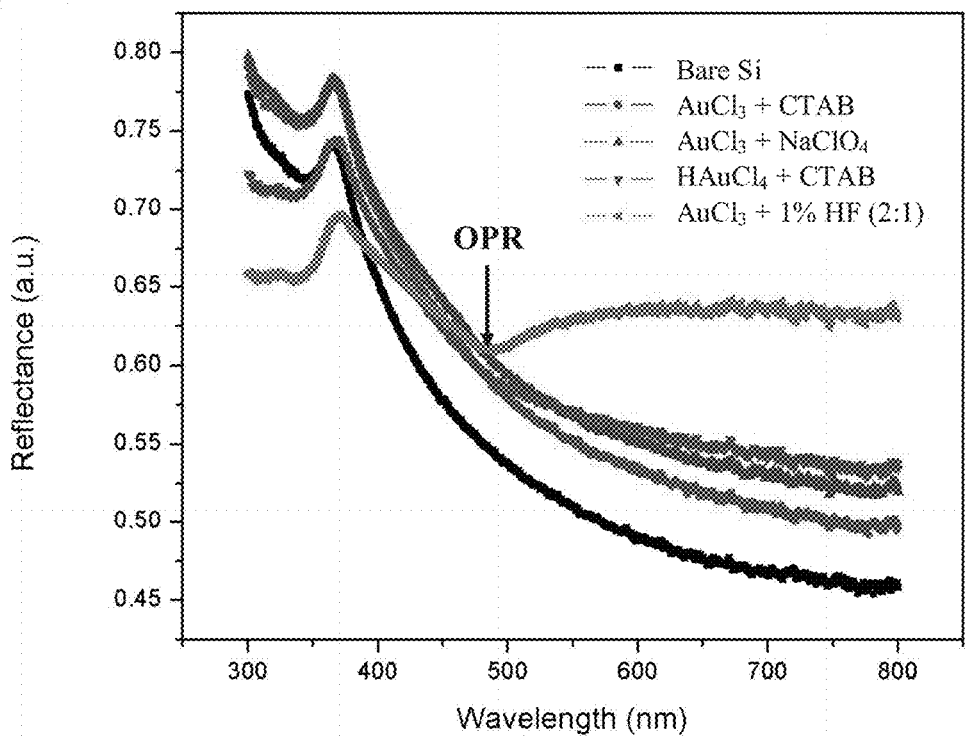
FIG. 22(a) shows the results of reflectance measurements of a silicon decorated with gold nanoparticles in a process of electroless deposition using different gold precursors.
Figure 22B:
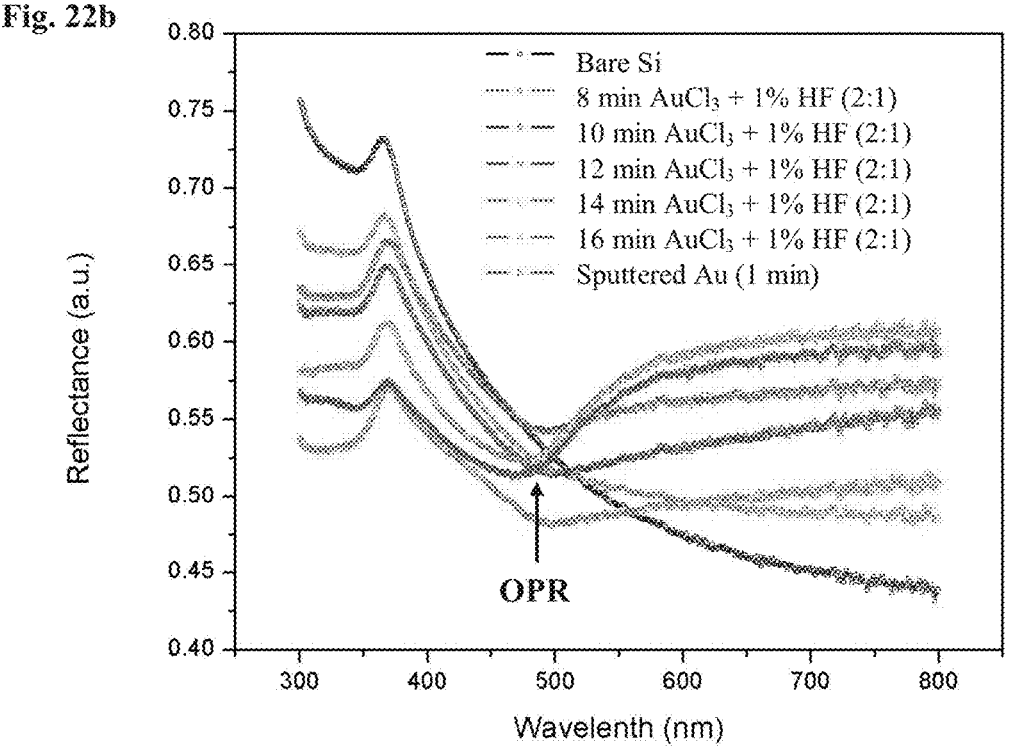
FIG. 22(b) shows the reflectance measurements of modified silicon as a function of the deposition reaction time.
Figure 22C:
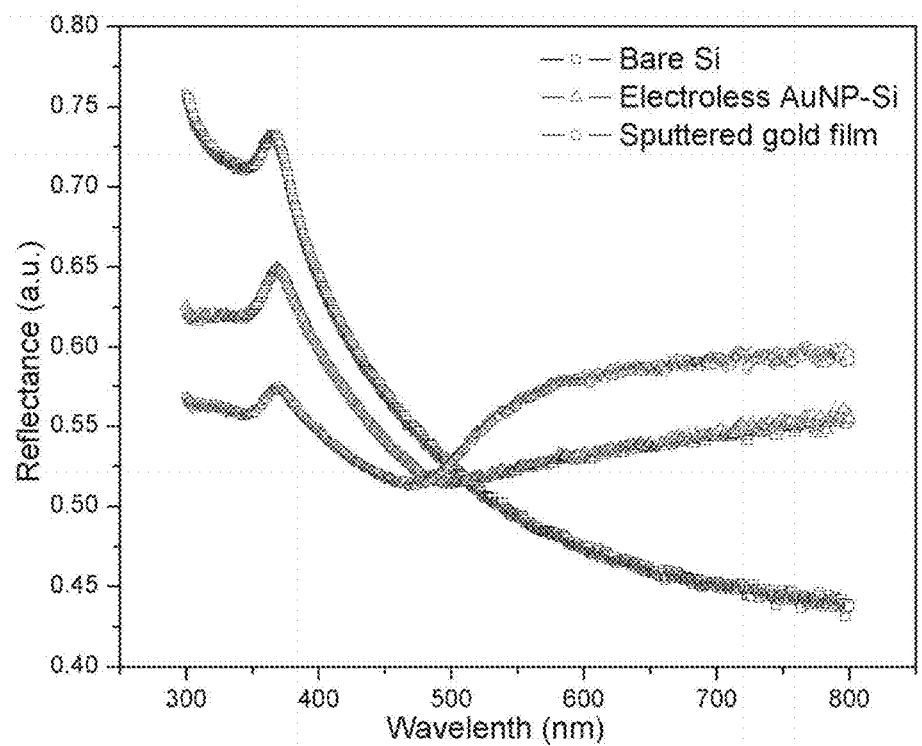
FIG. 22(c) shows the plasmonic response in the bare silicon, in the silicon electrolessly decorated with gold nanoparticles and in the silicon with a sputtered gold film.

FIGS. 22 (a)-(c) show experiments on reflectance measurements of a SiNW decorated with gold nanoparticles. FIG. 22 (a) demonstrates the search for the best system for measuring optoelectronic resonance (OPR). The resonance becomes clearly visible at 500-nm wavelength for the electrolessly deposited gold nanoparticles from the mixture of 1 mM $AuCl_3$ in 1% HF (2:1 v/v) in 15 minutes of the reaction. The gold salt precursor in FIG. 22 (a) was kept at the same concentration of 0.5 mM for 15 minutes of the reaction. As seen in this figure, other mixtures (with cetyltrimethylammonium bromide (CTAB) used to control nanoparticle size and shape, sodium perchlorate ($NaClO_4$) and isopropanol) were not indicative. This can be explained by low density of the deposited nanoparticles on the nanowire.

FIG. 22 (b) shows the reflectance measurements of a SiNW as a function of the deposition reaction time. The isosbestic point at 500 nm clearly indicates the resonance in the nanowires with the electrolessly deposited gold nanoparticles. As seen in the same picture, the resonance also appears at the same wavelength in gold films sputtered on silicon.

FIG. 22 (c) shows the plasmonic response in the SiNWs electrolessly decorated with gold nanoparticles and in the SiNW with a sputtered gold film. After close examination of the curves shown on FIG. 22 (c), the resonance wavelength was corrected to 470 nm, where light is absorbed the most.

Example 7: Sensing Biomolecules

Figure 23A:
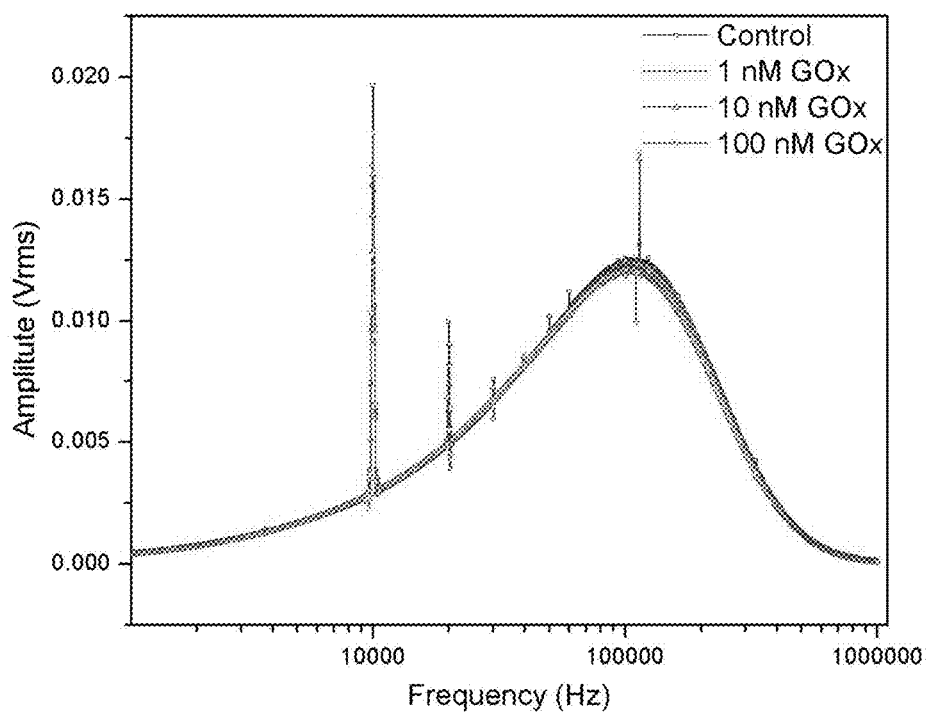
FIG. 23(a) shows the recorded spectrum for different concentration of GOx bound on the sensor chip of an embodiment measured at physiological conditioned solution (PBS 1×).
Figure 23B:
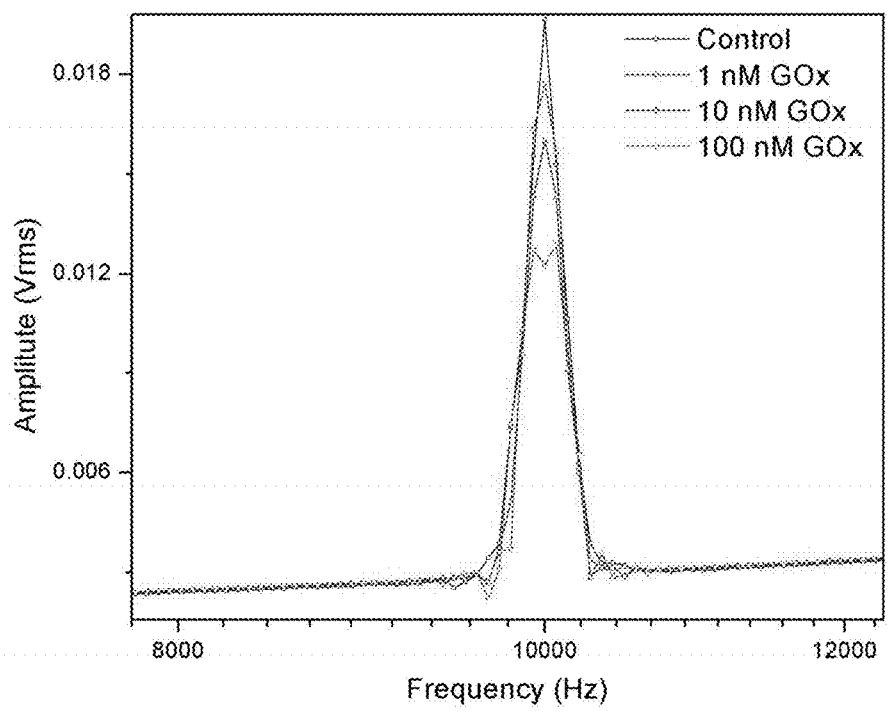
FIG. 23(b) shows the zoomed-in area of the 10-kHz resonance peak from the spectrum presented in FIG. 23(a).
Figure 23C:
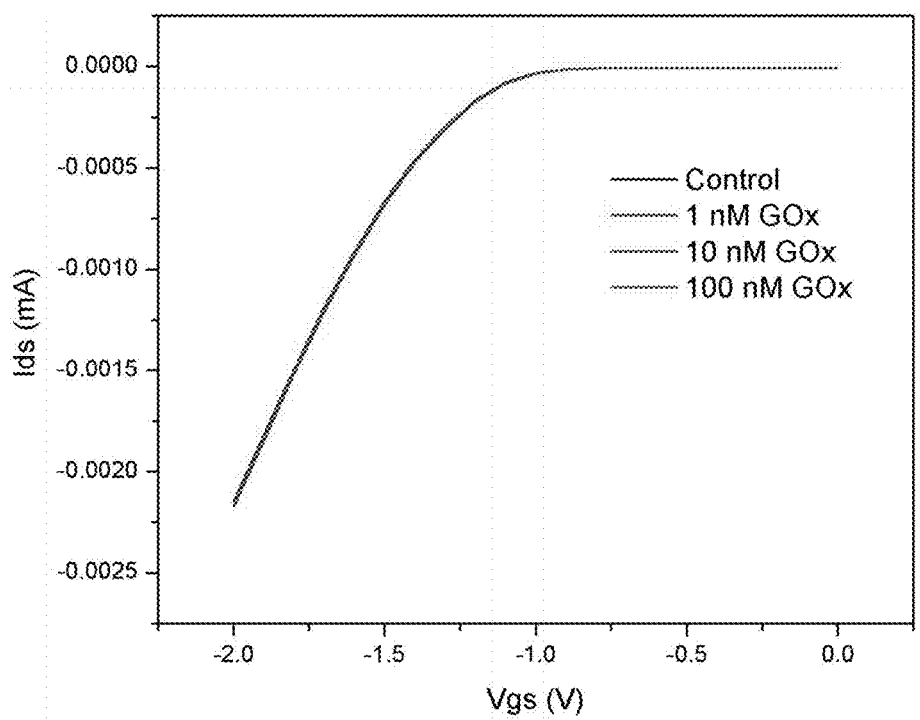
FIG. 23 (c) shows the DC readout of the same GOx system measured in PBS 1×.

The 10-kHz optoelectronic resonance in SiNWs was found to be sensitive to the presence of biomolecules on the surface of gold nanoparticles. Glucose oxidase (GOx) was used as a model for protein binding on the sensor chip of an embodiment. The sensor chip was irradiated with green light of 470 nm. FIG. 23 (a) shows the recorded spectrum for different concentration of GOx, while FIG. 23 (b) shows the zoomed-in area of the resonance peak in this spectrum. The amplitude change with varying concentration of GOx at the optoelectronic resonance frequency of 10 kHz is clearly observed.

For comparison, FIG. 23 (c) shows the DC readout of the same GOx system, where the change in the concentration of GOx is absolutely undetectable since it does not affect the drain-source current of the pixels. Moreover, as seen in FIG. 23 (a) the amplitude change at the optoelectronic resonance frequency of 10 kHz is much sharper and clearer than in conventional impedance resonance at 100 kHz.

Example 8: Pixels Decorated with ZnO Nanoclusters

Zinc oxide (ZnO) nanomaterials are known as highly favourable materials to increase the sensitivity, stability and durability of biosensor interfaces. ZnO possesses a high chemical stability, a wide direct band gap of 3.37 eV, a high refractive index of 2.0041 and a high electron mobility of 210 cm$^2$/Vs. It is especially suited for biosensor applications due to its low toxicity, high biocompatibility and high stability at physiological pH. It also has a high isoelectric point (IEP) of about 9.5, which facilitates a direct electron transfer (DET) in electrostatically adsorbing proteins with low IEPs. It has already been described that especially ZnO nanoclusters can facilitate the DET between the electroactive sites of enzymes and transducer electrodes.

Different nanostructured ZnO materials were used in the field to increase the response of mainly amperometric sensors based on metal (such as gold) electrodes or carbon-like materials such as graphene, carbon nanotubes and graphene oxide. These sensors showed remarkable potential for enzyme based biosensing including glucose, uric acid, L-lactic acid and cholesterol. For many of the investigated enzymes, hydrogen peroxide ($H_2O_2$) is one of the reaction products. Therefore, in enzyme-based bioassays, ZnO can be used to detect $H_2O_2$, when generated.

It has also been described that combinations of ZnO with Au can be used in Schottky barrier interfaces and can be exploited to facilitate a direct electron transfer between redox enzymes and transducers, thereby improving biosensor performance. Thus, ZnO nanoclusters can be used to decorate SiNW pixels to increase sensitivity of a transducer platform in a third-generation enzyme sensors exploiting the DET mechanisms.

The use of ZnO nanoclusters is particularly preferable for the direct 'wiring' of the redox-active centres of enzymes to electrode structures. The direct electron transfer then does not require any mediators in an analyte solution, and the substrate detection becomes independent of oxygen concentration (as in the first-generation enzyme sensors) or of the mediator concentration (as in the second-generation enzyme sensors).

In light of the above, the advantages of ZnO on the SiNW pixel platforms are manifold. The ZnO morphologies prepared from controlled synthesis possess large specific area. However, the actual structure, size and reproducibility of the nanostructures are very important in order to create highly reliable sensors in mass production. ZnO nanoclusters with high IEP promote the electrostatic adsorption of enzymes. Their biocompatibility retains the enzyme activity and the high crystallinity of ZnO nanoclusters provides the DET between the enzyme active sites and the silicon nanowires without requiring a mediator.

The most reliable and most controlled way to industrially upscale the fabrication of the ZnO nanoclusters on top-down fabricated SiNW pixel arrays is a method of atomic layer deposition (ALD). The following protocol was applied for the site-selective decoration of the silicon nanowires fabricated at the inventors' facility.

Si/ZnO hetero nanostructures were synthesized with a known protocol using low temperature ALD at growth temperature of 100 to 150° C. and a vacuum of 102 Torr depositing diethyl zinc and high-purity $H_2O$ as zinc and oxygen sources while nitrogen of 99.99% purity served as a carrier and purging gas. The pulses were of 0.015 sec and the gap between pulses was maintained at 10 sec. When grown at temperature of 115° C., growing with 20-80 pulses only, the produced seeds can catalyse the oxidation of hydrogen peroxide.

Figure 24:
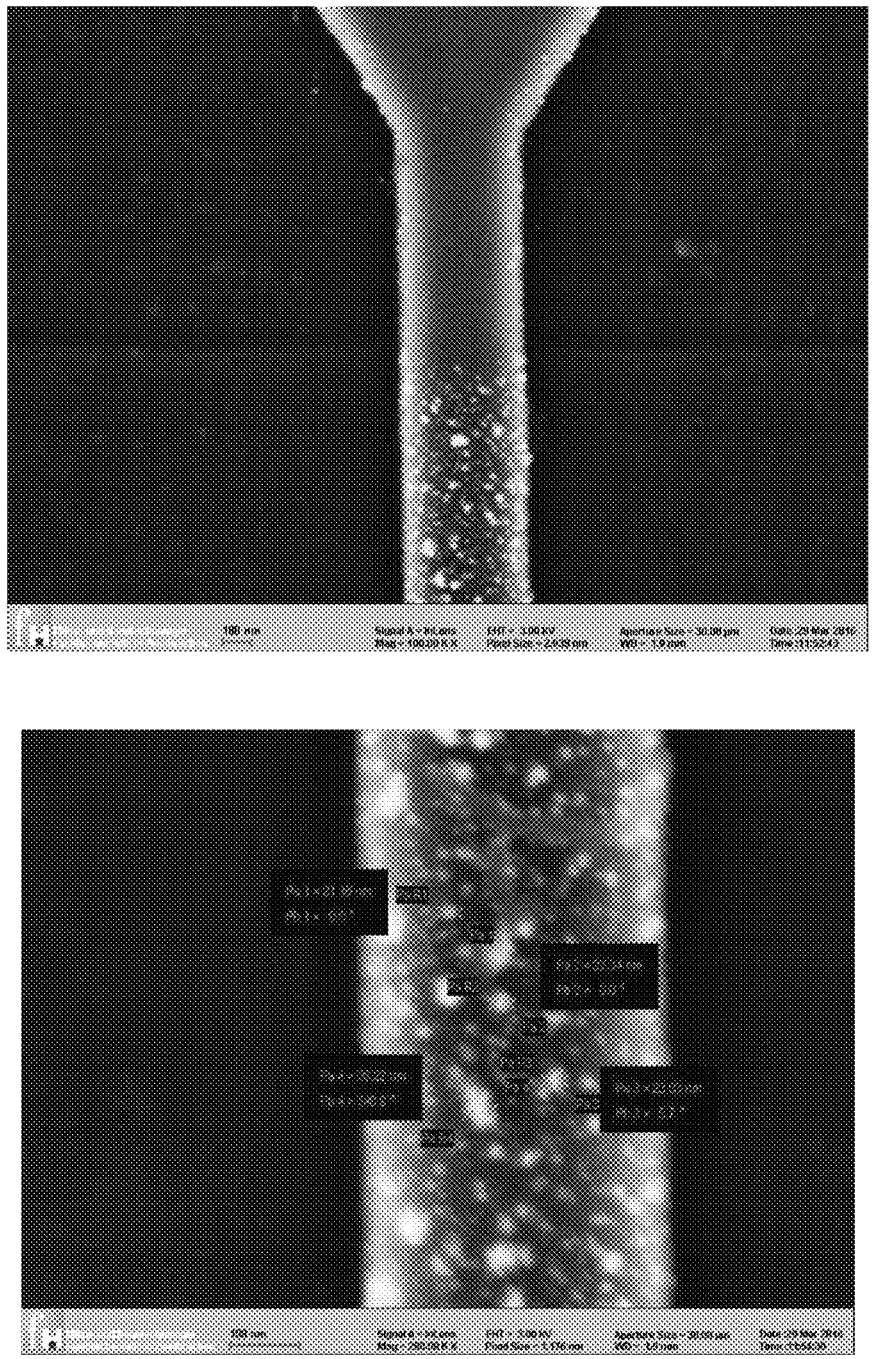
FIG. 24 shows the SEM images of the samples of ZnO nanoclusters deposited on a SiNW with 80 cycles of the ALD process.
Figure 25:
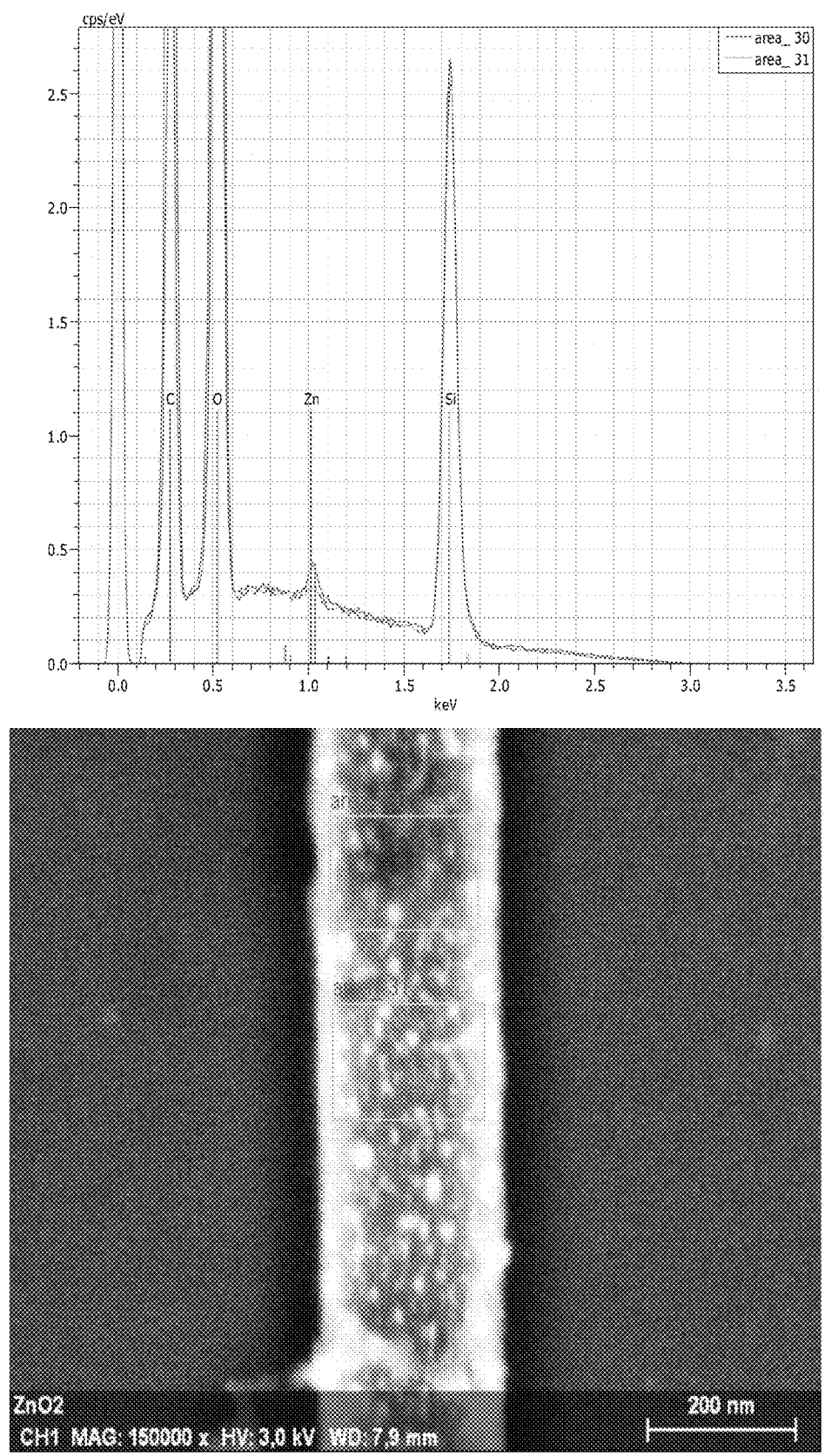
FIG. 25 shows the energy-dispersive X-ray spectrum (EDX) of the samples of ZnO nanoclusters deposited on a SiNW with 80 cycles of the ALD process.

FIG. 24 shows the SEM images of the samples of ZnO nanoclusters deposited on a SiNW with 80 cycles of the ALD process, while FIG. 25 shows the energy-dispersive X-ray spectrum (EDX) of the same hetero structures formed in the same 80 cycles of the ALD process. The sample was prepared using 115° C. with 80 cycles. ZnO nanoclusters of around 10-30 nm were identified on the SiNW. The contact lines were well passivated, and therefore, ZnO can only be found on the nanowire surface.

As shown in FIG. 25, two areas on the nanowire (Area 30 and Area 31) were analysed by the EDX. The sample was prepared using 115° C. with 80 cycles. Zn is detected with approximately 0.7% over the analysed area, while 48% of the spectrum detects Si. This clearly indicates that ZnO nanoclusters were formed on the surface instead of forming a complete thin layer of ZnO on Si.

Different concentrations of $H_2O_2$ were added to the sensor chip surface and a sweep of $V_{GS}$ (from 0 V to −1 V) at $V_{DS}$=−1 V was measured. All the $H_2O_2$ solutions measured in the experiment were prepared in 10 mM sodium phosphate buffer (pH 7.2). FIG. 26 shows the measurements of $H_2O_2$ at different concentrations conducted with the SiNW sensor pixel decorated with ZnO nanoclusters in (a) 10 cycles of the ALD process, and (b) 80 cycles of the same ALD process.

Figure 27:
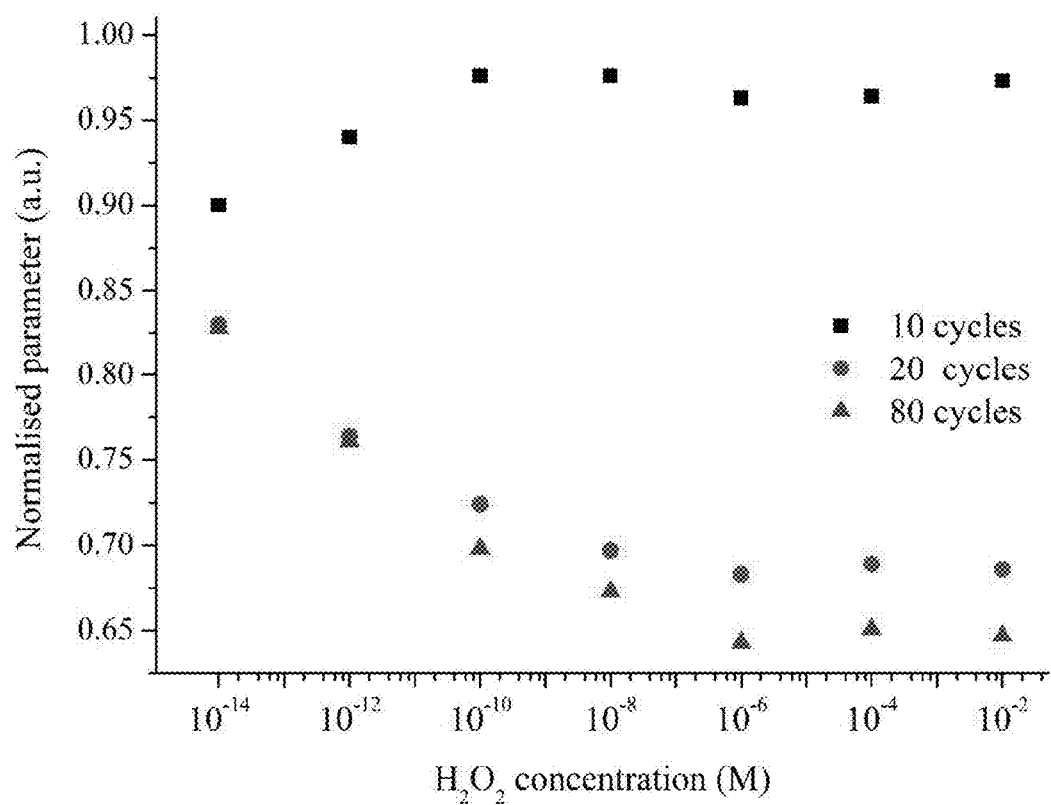
FIG. 27 shows the curves of the $I_{DS}$ normalised parameter vs concentration of $H_2O_2$ for 10, 20 and 80 cycles in the ALD process.

FIG. 27 shows the curves of the normalised parameter vs concentration of hydrogen peroxide for 10, 20 and 80 cycles in the ALD process. The "normalised parameter" is defined as a measured $I_{DS}$ value to baseline difference calculated for $V_{GS}$=−1 V for all cycles, followed by dividing the obtained values by their corresponding baseline values (in the absence of hydrogen peroxide). These normalised parameter values were plotted vs $H_2O_2$ concentration for different cycles to obtain the concentration-response curves. It is clearly seen from FIG. 27 that 10 cycles of the ALD process are insufficient to produce the linear response of the sensor of an embodiment. However, with 20 cycles of the ALD process and above, the amount of ZnO deposited on the sensor's surface allows the detection of $H_2O_2$ produced in the enzymatic reaction. The detection is also more sensitive for low concentrations of $H_2O_2$. The sensor becomes insensitive when the response reach the plateau values at approximately 1 μM $H_2O_2$ and above.

In conclusion, the array of the pixels decorated with ZnO nanoclusters offers now an industrially scalable platform for enzyme based detection of metabolites. Non-limiting examples of the metabolites are glucose, uric acid, L-lactic acid and cholesterol. The direct electron transfer mechanism is now also independent from the concentration of eventual mediators or of oxygen and could therefore be combined in one microfluidic container facilitating micro-spotting of different enzymes on different areas of the sensor pixel array. The assay is also ready for the use in patient samples such as human serum.

The invention claimed is:

1. An electrical circuit element, defined as an optoelectronic pixel, comprising:

at least one silicon nanowire (SiNW) decorated with optoelectronically active particles and open for contact with a medium;

a metal electrode open for contact with said medium for feeding a high-frequency sinusoidal AC stimulation in impedance measurements and for sensing properties of said medium, wherein said metal electrode is a temperature sensor, or both a counter electrode and temperature sensor, simultaneously;

implanted source and drain electrodes connected to said silicon nanowire and leaving a gate area of said pixel and parts of said metal electrode open for contact with said medium;

electrical metal contacts for connecting said electrical circuit element to an electrical circuit; and a reference electrode open for contact with said medium for creating a three-electrode-cell system and providing a constant potential in the circuit.

2. The optoelectronic pixel of claim 1, further comprising a backgate contact for the full electrostatic control of said optoelectronic pixel and for stabilising the electronic recording in electrolyte solutions.

3. The optoelectronic pixel of claim 1, wherein said optoelectronically active particles are metal nanoparticles, metal oxide nanostructures, or a combination thereof.

4. The optoelectronic pixel of claim 3, wherein said metal nanoparticles are made of Ag, Cu, Au, Al, Pd, Pt, Ni, Co, Pb, Ti, Fe or Cr.

5. The optoelectronic pixel of claim 3, wherein said metal oxide nanostructures are made of copper oxide (CuO), zinc oxide ($ZnO_2$), indium oxide ($In_2O_3$), tin oxide ($SnO_2$), indium zinc oxide (IZO), gallium zinc oxide (GZO), indium tin oxide (ITO), indium gallium zinc oxide (IGZO), indium zinc tin oxide (IZTO) or zinc tin oxide (ZTO).

6. The optoelectronic pixel of claim 1, wherein said silicon nanowire is low-doped p-type, low-doped n-type, drain n-doped and source p-doped, or drain p-doped and source n-doped.

7. The optoelectronic pixel of claim 1, wherein said metal electrode is a noble metal counter electrode.

8. The optoelectronic pixel of claim 7, wherein said noble metal is platinum, gold or copper.

9. The optoelectronic pixel of claim 1, wherein said reference electrode is an Ag/AgCl reference-cell electrode.

10. The optoelectronic pixel of claim 1, wherein said metal electrode and said reference electrode are not passivated and in direct contact with said medium.

11. The optoelectronic pixel of claim 1, further comprising a back gate at a bottom of said pixel for tuning a threshold voltage.

12. The optoelectronic pixel of claim 1, wherein the surface of said optoelectronically active particles is functionalised with receptor (capture) molecules capable of binding to target (analyte) molecules.

13. The optoelectronic pixel of claim 1, further comprising an excitation light source for irradiating said optoelectronically active particles, thereby creating plasmon resonance on the surface of said particles.

14. The optoelectronic pixel of claim 13, wherein said excitation light source is a laser diode or LED.

15. An optoelectronic sensor comprising a disposable unit mounted on a chip substrate, a reader unit mounted on a flexible printed circuit board (PCB), and an excitation light source, wherein:

said disposable unit comprises:
an array of pixels, each of claim 1, arranged in rows and columns and open for contact with a medium,
a row decoder connected to said array for addressing said pixels arranged in rows; and
a column decoder connected to said array for addressing said pixels arranged in columns; and said reader unit comprises:
a voltage source connected to an electric circuit for supplying electric power to the sensor;
an integrated or CMOS current amplifier connected to said array for amplification of an electric current obtained from said pixels;
an integrated function generator for modulating said light source;
a microcontroller with in-built digital input/output for processing and converting a received signal from said pixels into data readable in a user interface, and transmitting the converted signal to said user interface; and
a connection module for wired connection of the sensor to said user interface, or a wireless connection module for wireless connection of the sensor to said user interface.

16. The sensor of claim 15, wherein the surface of the optoelectronically active particles decorating the SiNW of each one of said pixels is functionalised with receptor (capture) molecules capable of binding to target (analyte) molecules in said medium.

17. The sensor of claim 15, wherein said wired connection module is USB, and said wireless connection module is NFC, GSM, Bluetooth® or Wi-Fi.

18. The sensor of claim 15, wherein said sensor further comprises a microfluidic chip or lateral flow strip for supplying an analyte solution to said electrical circuit elements array.

19. The sensor of claim 15, wherein said voltage source is a battery.

20. The sensor of claim 17, wherein said sensor is powered from said USB module.

21. The sensor of claim 15, wherein said sensor is powered wirelessly via an RFID (Radio-Frequency Identification) tag.

* * * * *

UNITED STATES PATENT AND TRADEMARK OFFICE
CERTIFICATE OF CORRECTION

PATENT NO.       : 10,054,563 B2
APPLICATION NO.  : 15/087866
DATED            : August 21, 2018
INVENTOR(S)      : Ayal Ram et al.

Page 1 of 1

It is certified that error appears in the above-identified patent and that said Letters Patent is hereby corrected as shown below:

On the Title Page

Item (73), Assignee at Line 1, Change "RGE" to --RG--.

Signed and Sealed this
Ninth Day of October, 2018

Andrei Iancu
*Director of the United States Patent and Trademark Office*